(12) United States Patent
Xia et al.

(10) Patent No.: US 11,896,404 B2
(45) Date of Patent: Feb. 13, 2024

(54) SYSTEMS AND METHODS FOR MEDICAL IMAGING OF A HEART AND ANALYSIS OF ECG TARGET CHANNEL

(71) Applicant: SHANGHAI UNITED IMAGING HEALTHCARE CO., LTD., Shanghai (CN)

(72) Inventors: Xiang Xia, Shanghai (CN); Zhongling Guan, Shanghai (CN); Zhaolong Zeng, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 135 days.

(21) Appl. No.: 17/138,962

(22) Filed: Dec. 31, 2020

(65) Prior Publication Data

US 2021/0121134 A1 Apr. 29, 2021

(30) Foreign Application Priority Data

Dec. 31, 2019 (CN) .......................... 201911421232.3
Sep. 14, 2020 (CN) .......................... 202010962025.5

(51) Int. Cl.
*A61B 5/00* (2006.01)
*G06T 11/00* (2006.01)
(Continued)

(52) U.S. Cl.
CPC .............. *A61B 5/7285* (2013.01); *A61B 5/31* (2021.01); *A61B 5/318* (2021.01); *A61B 5/347* (2021.01);
(Continued)

(58) Field of Classification Search
CPC ......... A61B 5/7285; A61B 5/31; A61B 5/318; A61B 5/347; A61B 5/055; A61B 6/032;
(Continued)

(56) References Cited

U.S. PATENT DOCUMENTS 5,146,926 A 9/1992 Cohen
6,285,188 B1 9/2001 Sakakura
(Continued)

FOREIGN PATENT DOCUMENTS

CN 1660011 A 8/2005
CN 101191830 A 6/2008
(Continued)

OTHER PUBLICATIONS

First Office Action in Chinese Application No. 201911421232.3 dated Apr. 20, 2022, 16 pages.
(Continued)

*Primary Examiner* — Serkan Akar
*Assistant Examiner* — Gabriel Victor Popescu
(74) *Attorney, Agent, or Firm* — METIS IP LLC

(57) ABSTRACT

The present disclosure provides systems and methods for medical imaging. The method may include obtaining a plurality of channels of electrocardiogram (ECG) signals of a heart of a subject; identifying, from the plurality of channels of ECG signals, a target channel of ECG signal, wherein an amplitude of a characteristic wave of the target channel of ECG signal is the maximum amplitude among amplitudes of corresponding characteristic waves of the plurality of channels of ECG signals; and causing, based on the target channel of ECG signal, an imaging device to perform a scan operation on the heart of the subject.

17 Claims, 13 Drawing Sheets

(51) Int. Cl.
*A61B 5/318* (2021.01)
*A61B 5/31* (2021.01)
*A61B 5/347* (2021.01)
*A61B 6/00* (2006.01)
*A61B 6/03* (2006.01)
*A61B 5/055* (2006.01)
*A61B 8/08* (2006.01)

(52) U.S. Cl.
CPC ............. *G06T 11/006* (2013.01); *A61B 5/055* (2013.01); *A61B 6/032* (2013.01); *A61B 6/037* (2013.01); *A61B 6/4447* (2013.01); *A61B 8/0883* (2013.01); *G06T 2210/41* (2013.01)

(58) Field of Classification Search
CPC ..... A61B 6/037; A61B 6/4447; A61B 8/0883; A61B 5/349; A61B 6/03; A61B 6/503; A61B 6/5288; A61B 5/352; A61B 5/7225; A61B 6/4417; A61B 8/5284; A61B 6/541; G06T 11/006; G06T 2210/41
See application file for complete search history.

(56) References Cited

U.S. PATENT DOCUMENTS

| | | | |
|---|---|---|---|
| 6,358,214 B1* | 3/2002 | Tereschouk | A61B 5/318 600/508 |
| 8,332,042 B2* | 12/2012 | Williams | A61N 1/05 607/115 |
| 9,872,987 B2* | 1/2018 | Libbus | A61N 1/3611 |
| 2009/0060120 A1* | 3/2009 | Mukumoto | A61B 6/503 378/8 |
| 2010/0040193 A1 | 2/2010 | Lessick | |
| 2011/0033097 A1* | 2/2011 | Bruder | G06T 11/006 382/131 |
| 2016/0310037 A1 | 10/2016 | O'Neill et al. | |
| 2017/0086771 A1* | 3/2017 | Yasuhiro | A61B 6/032 |
| 2017/0087364 A1* | 3/2017 | Cartledge | A61N 1/36034 |
| 2018/0214110 A1* | 8/2018 | Igarashi | A61B 6/5288 |
| 2019/0133485 A1* | 5/2019 | Volpe | A61B 5/341 |
| 2019/0139275 A1* | 5/2019 | Hao | G06T 2210/41 |
| 2020/0022608 A1 | 1/2020 | Sha | |

FOREIGN PATENT DOCUMENTS

| | | |
|---|---|---|
| CN | 102551702 A | 7/2012 |
| CN | 103050265 A | 4/2013 |
| CN | 103431856 A | 12/2013 |
| CN | 203354539 U | 12/2013 |
| CN | 104757963 A | 7/2015 |
| CN | 106264517 A | 1/2017 |
| CN | 107749674 A | 3/2018 |
| CN | 109124622 A | 1/2019 |
| CN | 109893117 A | 6/2019 |
| CN | 209032349 U | 6/2019 |
| CN | 110403597 A | 11/2019 |
| CN | 211658147 U | 10/2020 |
| JP | 2002202328 A | 7/2002 |
| JP | 2011200268 A | 10/2011 |

OTHER PUBLICATIONS

Yang, Wei et al., A Kind of High-field MRI Compatible ECG Acquisition and Processing System Design, Life Science Instruments, 2015, 6 pages.

First Office Action in Chinese Application No. 202011638649.8 dated Aug. 31, 2022, 19 pages.

* cited by examiner

1300

1400

SYSTEMS AND METHODS FOR MEDICAL IMAGING OF A HEART AND ANALYSIS OF ECG TARGET CHANNEL

CROSS-REFERENCE TO RELATED APPLICATIONS

This application claims priority of Chinese Patent Application No. 202010962025.5, filed on Sep. 14, 2020, and Chinese patent Application No. 201911421232.3, filed on Dec. 31, 2019, the contents of each of which are hereby incorporated by reference.

TECHNICAL FIELD

The disclosure generally relates to medical imaging, and more particularly relates to systems and methods for determining a gating signal for scanning a heart of a subject.

BACKGROUND

A medical imaging device, such as a computed tomography (CT) device, a positron emission tomography (PET) device, a magnetic resonance imaging (MRI) device, an ultrasound scanning device, etc., is widely used in the field of disease diagnosis. For example, the CT device may scan a heart of a subject (e.g., a human or an animal), and generate scan data. The CT device may reconstruct a cardiac image of the heart based on the scan data. However, a cardiac motion during the CT scan can cause resolution degradation and introduce artifacts in the cardiac image that affect diagnoses performed on the basis of the cardiac image. For example, the cardiac motion leads to motion artifacts and blurring in the cardiac image, which hinders an accurate detection, localization, and quantification of possible lesions and tumors. In order to reduce or eliminate cardiac image degradation induced by cardiac motion, heart scan may be performed at time phases when the cardiac motion amplitude is relatively small, and accordingly, a gating signal associated with the cardiac motion is required for heart scans. Thus, it is desirable to develop systems and methods for determining an accurate gating signal, thereby improving scanning efficiency and/or reducing the radiation dose received by the subject.

SUMMARY

According to an aspect of the present disclosure, a system for medical imaging is provided. The system may include at least one storage device storing executable instructions, and at least one processor in communication with the at least one storage device. When executing the executable instructions, the at least one processor may be configured to direct the system to perform one or more of the following operations. The system may obtain a plurality of channels of electrocardiogram (ECG) signals of a heart of a subject. The system may further identify, from the plurality of channels of ECG signals, a target channel of ECG signal. An amplitude of a characteristic wave of the target channel of ECG signal may be the maximum amplitude among amplitudes of corresponding characteristic waves of the plurality of channels of ECG signals. The system may further cause, based on the target channel of ECG signal, an imaging device to perform a scan operation on the heart of the subject.

In some embodiments, to identify, from the plurality of channels of ECG signals, a target channel of ECG signal, the at least one processor may be configured to direct the system to perform one or more of the following operations. The system may perform a preprocessing operation on each of the plurality of channels of ECG signals. The system may further determine, from the plurality of channels of preprocessed ECG signals, the target channel of ECG signal.

In some embodiments, the preprocessing operation may include at least one of an amplifying operation or a filtering operation.

In some embodiments, to cause, based on the target channel of ECG signal, an imaging device to perform a scan operation on the heart of the subject, the at least one processor may be configured to direct the system to perform one or more of the following operations. The system may generate, based on the target channel of ECG signal, a gating signal. The system may cause, based on the gating signal, the imaging device to perform the scan operation on the heart of the subject.

In some embodiments, to generate, based on the target channel of ECG signal, a gating signal, the at least one processor may be configured to direct the system to perform one or more of the following operations. The system may detect the characteristic wave of the target channel of ECG signal. The system may generate, based on the characteristic wave of the target channel of ECG signal, the gating signal.

In some embodiments, the at least one processor may be further configured to cause the system to perform one or more of the following operations. The system may determine, based at least in part on the plurality of channels of ECG signals, a heart disorder of the heart. The system may further determine, based on the heart disorder of the heart, a target time phase. The system may further determine, based on the target time phase, a gating delay and a gating width. To cause, based on the gating signal, the imaging device to perform the scan operation on the heart of the subject, the at least one processor may be configured to cause the system to cause, based on the gating signal, the gating delay, and the gating width, the imaging device to perform the scan operation on the heart of the subject.

In some embodiments, to determine, based at least in part on the plurality of channels of ECG signals, a heart disorder of the heart, the at least one processor may be configured to cause the system to determine one or more features of the plurality of channels of ECG signals. The system may further determine, based at least in part on the one or more features, the heart disorder of the heart.

In some embodiments, to determine, based on the heart disorder of the heart, a target time phase, the at least one processor may be configured to cause the system to query a library based on the heart disorder of the heart. The library may include a relationship between the heart disorder of the heart and the target time phase. The system may further determine the target time phase based on the query result.

In some embodiments, to determine, based on the target time phase, a gate delay and a gating width, the at least one processor may be configured to cause the system to obtain a plurality of durations corresponding to a plurality of previous cardiac cycles before a current cardiac cycle. The system may further determine an average duration of the plurality of durations corresponding to the plurality of previous cardiac cycles. The system may further determine, based on the average duration and the target time phase, the gating delay and the gating width.

In some embodiments, the at least one processor may be further configured to cause the system to perform one or more of the following operations. The system may obtain a plurality of channels of second ECG signals monitored during the scan operation. The system may determine, based at least in part on the second ECG signals, an updated heart disorder of the heart. The system may further update, based on the updated heart disorder of the heart, the target time phase.

In some embodiments, a retrospective ECG gating may be used in the scan operation. The at least one processor may be further configured to cause the system to perform one or more of the following operations. The system may obtain scan data generated in the scan operation. The system may further obtain, from the target channel, a second ECG signal monitored during the scan operation. The system may further reconstruct a cardiac image based on the scan data and the second ECG signal.

In some embodiments, a retrospective ECG gating may be used in the scan operation. The at least one processor may be further configured to cause the system to perform one or more of the following operations. The system may obtain scan data generated in the scan operation. The system may obtain a plurality of channels of second ECG signals monitored during the scan operation. The system may further reconstruct a cardiac image based on the scan data and the second ECG signals.

In some embodiments, to reconstruct a cardiac image based on the scan data and the second ECG signals, the at least one processor may be configured to cause the system to perform one or more of the following operations. The system may determine, based at least in part on the second ECG signals, a heart disorder of the heart. The system may determine, based on the heart disorder of the heart, a target time phase. The system may determine, from the scan data, target scan data corresponding to the target time phase. The system may reconstruct, based on the target scan data, the cardiac image.

In some embodiments, the at least one processor may be further configured to cause the system to perform one or more of the following operations. The system may obtain a plurality of channels of second ECG signals monitored during the scan operation. The system may further determine, based on the second ECG signals, an updated target channel of ECG signal. The system may further operate, based on the updated target channel of ECG signal, the imaging device to perform the scan operation on the heart.

In some embodiments, the at least one processor may be further configured to cause the system to prompt a user that the target channel of ECG signal is updated.

In some embodiments, the plurality of channels of electrocardiogram (ECG) signals may be detected by a multi-lead sensing device.

In some embodiments, the multi-lead sensing device may include one or more electrodes. At least one of the one or more electrodes may include an electrode clamp and an electrode wire. The electrode wire may be winded to form one or more first coils and one or more second coils. A first winding direction of each of the one or more first coils may be different from a second winding direction of each of the one or more second coils.

According to another aspect of the present disclosure, a system for medical imaging is provided. The system may include at least one storage device storing executable instructions, and at least one processor in communication with the at least one storage device. When executing the executable instructions, the at least one processor may be configured to direct the system to perform one or more of the following operations. The system may obtain scan data generated by scanning a heart of a subject using an imaging device. The system may further obtain a plurality of channels of electrocardiogram (ECG) signals of the subject that are monitored during the scanning of the heart. The system may further identify, from the plurality of channels of ECG signals, a target channel of ECG signal. An amplitude of a characteristic wave of the target channel of ECG signal may be the maximum amplitude among amplitudes of corresponding characteristic waves of the plurality of channels of ECG signals. The system may further reconstruct one or more cardiac images based on the scan data and the target channel of ECG signal.

In some embodiments, the at least one processor may be further configured to cause the system to perform one or more of the following operations. The system may determine, based at least in part on the plurality of channels of ECG signals, a heart disorder of the heart. The system may further determine, based on the heart disorder of the heart, a target time phase. To reconstruct one or more cardiac images based on the scan data and the target channel of ECG signal, the at least one processor may be configured to cause the system to perform one or more of the following operations. The system may determine, from the scan data, target scan data corresponding to the target time phase. The system may further reconstruct, based on the target scan data, the cardiac image.

According to yet another aspect of the present disclosure, a gating system is provided. The system may include at least one storage device storing executable instructions, and at least one processor in communication with the at least one storage device. When executing the executable instructions, the at least one processor may be configured to direct the system to perform one or more of the following operations. The system may obtain a plurality of channels of electrocardiogram (ECG) signals of a heart of a subject. The system may identify, from the plurality of channels of ECG signals, a target channel of ECG signal. An amplitude of a characteristic wave of the target channel of ECG signal may be the maximum amplitude among amplitudes of corresponding characteristic waves of the plurality of channels of ECG signals. The system may generate, based on the target channel of ECG signal, a gating signal.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
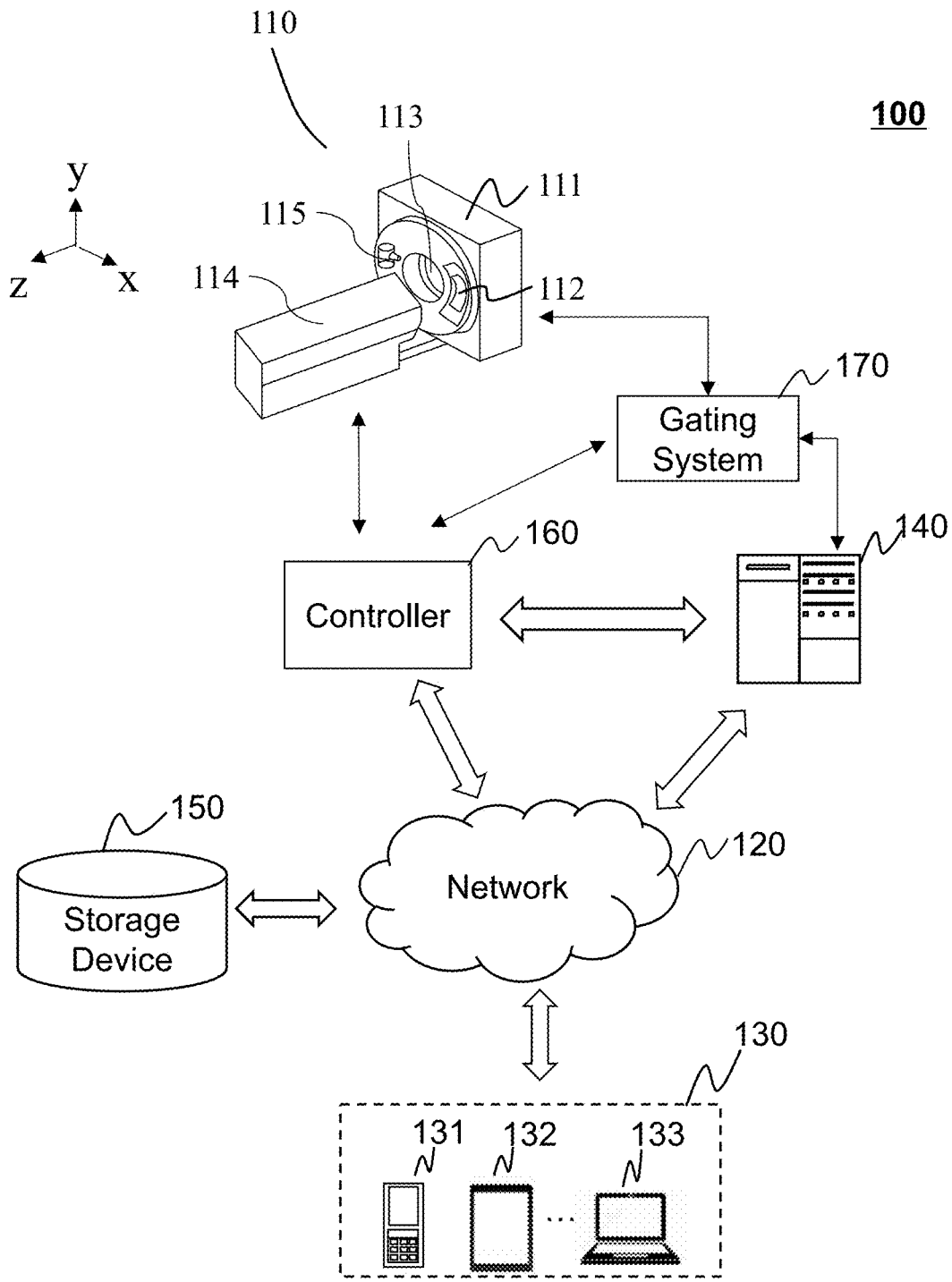
FIG. 1 is a schematic diagram illustrating an exemplary imaging system according to some embodiments of the present disclosure.

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown but is to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including" when used in this disclosure, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections, or assembly of different levels in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage devices. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an erasable programmable read-only memory (EPROM). It will be further appreciated that hardware modules/units/blocks may be included in connected logic components, such as gates and flip-flops, and/or can be included in programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module, or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments in the present disclosure. It is to be expressly understood, the operations of the flowchart may be implemented not in order. Conversely, the operations may be implemented in inverted order, or simultaneously. Moreover, one or more other operations may be added to the flowcharts. One or more operations may be removed from the flowcharts.

For illustration purposes, the following description is provided to help better understanding an imaging process. It is understood that this is not intended to limit the scope of the present disclosure. For persons having ordinary skills in the art, a certain amount of variations, changes, and/or modifications may be deducted under the guidance of the present disclosure. Those variations, changes, and/or modifications do not depart from the scope of the present disclosure.

The term "image" in the present disclosure is used to collectively refer to image data (e.g., scan data, projection data) and/or images of various forms, including a two-dimensional (2D) image, a three-dimensional (3D) image, a four-dimensional (4D), etc. The term "pixel" and "voxel" in the present disclosure are used interchangeably to refer to an element of an image. The term "region," "location," and "area" in the present disclosure may refer to a location of an anatomical structure shown in the image or an actual location of the anatomical structure existing in or on a target subject's body, since the image may indicate the actual location of a certain anatomical structure existing in or on the target subject's body.

The present disclosure relates to systems and methods for medical imaging and/or gating systems associated with medical imaging. In some embodiments, the system may obtain a plurality of channels of electrocardiogram (ECG) signals of a heart of a subject. The system may identify, from the plurality of channels of ECG signals, a target channel of ECG signal. An amplitude of a characteristic wave of the target channel of ECG signal may be the maximum amplitude among amplitudes of corresponding characteristic waves of the plurality of channels of ECG signals. The system may cause, based on the target channel of ECG signal, an imaging device to perform a scan operation on the heart of the subject.

In traditional heart scans, gating signals generated based on a predetermined channel (e.g., a prescribed channel used for different hearts in different scan operations and regardless of heart conditions) of ECG signal can be used for triggering scan operation or image reconstruction. However, in some embodiments, the predetermined channel of ECG signal may be unavailable (e.g., unusable, or difficult to identify), and thus affecting heart scan results or image reconstruction results. According to the systems and methods of the present disclosure, when the predetermined channel of ECG signal is detected to be unavailable in the scan operation (or before the scan operation), the systems and methods may automatically switch to another channel of ECG signal (e.g., the target channel of ECG signal) that is useable. Accordingly, by identifying the target channel of ECG signal from the plurality of channels of ECG signals, the scanning efficiency may be improved, repeated scanning may be reduced or avoided, and thus, the radiation dose received by the subject may be reduced. For example, if a prospective gating is used in the scan operation, and when the predetermined channel of ECG signal is unavailable, the predetermined channel may be switched to the target channel automatically. In such cases, there is no need to rescan the subject, thereby reducing the radiation dose received by the subject and improving the scanning efficiency. As another example, if a retrospective gating is used, and when the predetermined channel of ECG signal is unavailable, the predetermined channel may be switched to the target channel automatically, or the plurality of channels of ECG signals may be monitored simultaneously during the scan operation. In such cases, when reconstructing a cardiac image of the heart, a user (e.g., a doctor) may easily select target scan data from scan data generated during the scan operation based on the target channel of ECG signal, thereby reducing the time required for reconstruction and improving image reconstruction efficiency and accuracy.

FIG. 1 is a schematic diagram illustrating an exemplary imaging system according to some embodiments of the present disclosure. An imaging system 100 may acquire an image of a subject. As illustrated in FIG. 1, the imaging system 100 may include an imaging device 110, a network 120, a terminal device 130, a processing device 140, a storage device 150, a controller 160, and/or a gating system 170.

The imaging device 110 may be configured to acquire scan data relating to at least part of a subject (e.g., the heart of the subject). The subject may include a patient or an animal. In some embodiments, the heart of the subject may be an artificial heart. In some embodiments, the imaging device 110 may include a computed tomography (CT) device, an emission computed tomography (ECT) device, a magnetic resonance imaging (MRI) device, a positron emission tomography (PET) device, a single-photon emission computed tomography (SPECT) device, an ultrasound scanning device, an X-ray imaging device, a PET-CT device, or the like, or any combination thereof. In some embodiments, the imaging device 110 may be a radiation imaging device. The radiation imaging device may include a radiation source to emit radioactive rays to the subject to be scanned. The radioactive rays may include, for example, particle rays, photon rays, or the like, or any combination thereof. The particle rays may include neutrons, protons, electrons, p-mesons, heavy ions, or the like, or any combination thereof. The photon rays may include X-ray, y-ray, a-ray, p-ray, ultraviolet, laser, or the like, or any combination thereof.

In some embodiments, the imaging device 110 may be a CT imaging device including a gantry 111, a detector 112, a field of view (FOV) 113, a table 114, and a radiation source 115. The gantry 111 may support the detector 112 and the radiation source 115. The subject may be placed on the table 114 and moved into the FOV 113 for scanning along the z-axis as illustrated in FIG. 1. The radiation source 115 may emit radioactive rays to the subject. The detector 112 may detect radiation events (e.g., radiation attenuation, gamma photons emitted from the FOV 113). In some embodiments, the detector 112 may include one or more detector units. The detector 112 may include a scintillation detector (e.g., a cesium iodide detector), a gas detector, etc. The detector 112 may be and/or include a single-row detector in which a plurality of detector units are arranged in a single row and/or a multi-row detector in which a plurality of detector units are arranged in multiple rows.

The network 120 may include any suitable network that can facilitate the exchange of information and/or data for the imaging system 100. In some embodiments, one or more components (e.g., the imaging device 110, the processing device 140, the storage device 150, or the terminal device 130) of the imaging system 100 may communicate information and/or data with one or more other components of the imaging system 100 via the network 120. For example, the processing device 140 may obtain scan data from the imaging device 110 via the network 120. As another example, the processing device 140 may obtain user instructions from the terminal device 130 via the network 120. The network 120 may include a public network (e.g., the Internet), a private network (e.g., a local area network (LAN), a wide area network (WAN), etc.), a wired network (e.g., an Ethernet), a wireless network (e.g., an 802.11 network, a wireless Wi-Fi network, etc.), a cellular network (e.g., a long term evolution (LTE) network), a frame relay network, a virtual private network (VPN), a satellite network, a telephone network, routers, hubs, server computers, and/or any combination thereof. For example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the imaging system 100 may be connected to the network 120 to exchange data and/or information.

The terminal device 130 may be connected to and/or communicate with the imaging device 110, the processing device 140, and/or the storage device 150. For example, the terminal device 130 may enable user interactions between a user and the imaging system 100. For example, the user may instruct the imaging device 110 to acquire scan data or instruct the processing device 140 to process scan data via the terminal device 130. In some embodiments, the terminal device 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. In some embodiments, the smart home device may include a smart lighting device, a smart electrical appliance control device, a smart monitoring device, a smart TV, a smart camera, a walkie-talkie, or the like, or any combination thereof. In some embodiments, the wearable device may include bracelets, footwear, glasses, helmets, watches, clothes, backpacks, smart accessories, or the like, or any combination thereof. In some embodiments, the mobile device may include a mobile phone, a personal digital assistant (PDA), a game device, a navigation device, a POS device, a notebook computer, a tablet computer, a desktop computer, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or augmented reality device may include Google Glass™, Oculus Rift™, HoloLens™, Gear VR™, or the like. In some embodiments, the terminal device 130 may be part of the processing device 140.

The processing device 140 may process data and/or information obtained from the imaging device 110, the terminal device 130, the storage device 150, the controller 160 and/or the gating system 170. For example, the processing device 140 may identify a target channel of ECG signal from a plurality of channels of ECG signals of the subject. The processing device 140 may cause the imaging device 110 to perform a scan operation on the heart of the subject based on the target channel of ECG signal. As another example, the processing device 140 may reconstruct a cardiac image of the subject based on scan data of the heart and the target channel of ECG signal monitored during the scan operation. In some embodiments, the processing device 140 may be a computer, a user console, a single server or a server group, etc. The server group can be centralized or distributed. In some embodiments, the processing device 140 may be local to or remote from the imaging system 100. For example, the processing device 140 may access information and/or data from the imaging device 110, the storage device 150, and/or the terminal device 130 via the network 120. As another example, the processing device 140 may be directly connected to the imaging device 110, the terminal device 130, and/or the storage device 150 to access information and/or data. In some embodiments, the processing device 140 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 140 may be implemented by a computing device 200 having one or more components as described in connection with FIG. 2 in the present disclosure.

The storage device 150 may store data, instructions, and/or any other information. In some embodiments, the storage device 150 may store data obtained from the imaging device 110, the terminal device 130, and/or the processing device 140. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform as described elsewhere in the disclosure.

In some embodiments, the storage device 150 may be connected to the network 120 to communicate with one or more other components (e.g., the processing device 140, the terminal device 130) of the imaging system 100. One or more components of the imaging system 100 may access the data or instructions stored in the storage device 150 via the network 120. In some embodiments, the storage device 150 may be part of the processing device 140, or directly or indirectly connected to the processing device 140.

The controller 160 may control the imaging device 110, and/or the processing device 140. In some embodiments, the controller 160 may control a radiation source and/or a detector of the imaging device 110. The controller 160 may receive information from or send information to the imaging device 110, the terminal device 130, and/or the processing device 140. For example, the controller 160 may receive commands from the terminal device 130 provided by a user. As another example, the controller 160 may control the imaging device 110, the terminal device 130, and/or the processing device 140 according to the received commands or transformed commands. As a further example, the controller 160 may send image signals or data to the processing device 140. In some embodiments, the controller 160 may include a computer, a program, an algorithm, a software, a storage device, one or more interfaces, etc. Exemplary interfaces may include the interfaces with the imaging device 110, the processing device 140, and/or other modules or units in the imaging system 100. In some embodiments, the controller 160 may be part of the processing device 140.

In some embodiments, the controller 160 may receive a command provided by a user (e.g., an imaging technician, a doctor, etc.). Exemplary commands may relate to a scan time, a location of the subject, the location of a table on which the subject lies, a specific parameter relating to a threshold that may be used in the image reconstruction process, or the like, or any combination thereof. In some embodiments, the controller 160 may control the processing device 140 to select different algorithms to process the raw data of an image.

The gating system 170 may collect information relating to the heartbeat and/or generate a gating signal based on the collected information. The collected information may include a cardiac motion signal. In some embodiments, the cardiac motion signal may include an ECG signal. The ECG signal may indicate and/or record the heartbeats of the subject during the scan operation. For example, the ECG signal may indicate information related to the heartbeats, for example, a cardiac cycle, a heart rate, an activation condition of atrium(s) and/or ventricle(s), etc. In some embodiments, the gating system 170 may include an ECG signal detector, a control panel, etc. Exemplary ECG signal detectors may include one or more sensors (e.g., electrodes), one or more amplifying circuits, one or more filtering circuits, or the like, or any combination thereof. In some embodiments, when the imaging device 110 is scanning a subject (e.g., a patient), the gating system 170 may be started automatically. The gating system 170 may collect information (e.g., different channels of ECG signals) associated with the cardiac motion of the heart of the subject during the scanning. The data (e.g., data associated with ECG signals) collected by the gating system 170 may be stored together with the scan data generated in a scan operation(s) of the imaging device 110. In some embodiments, the gating system 170 may transmit a gating signal to the controller 160, and the controller 160, after receiving the gating signal, may selectively turns the imaging device 110 on and off. For example, the controller 160 may gate the radiation source 115 of the CT device (e.g., based on the gating signal provided by the gating system 170) to selectively turn the radiation source 115 on and off during the scan operation of the heart of the subject, so that, for each scan, radiation is only emitted at certain acquisition time phases in an acquisition window (also referred to as a gating width).

In some embodiments, the imaging device 110, the terminal device 130, the processing device 140, the controller 160, and the gating system 170 may be connected to or communicate with each other directly. In some embodiments, the imaging device 110, the terminal device 130, the processing device 140, the controller 160, and the gating system 170 may be connected to or communicate with each other via a network 120. In some embodiments, the gating system 170 and/or the controller 160 may be part of the imaging device 110.

It should be noted that the above description of the imaging system 100 is merely provided for the purposes of illustration, and not intended to limit the scope of the present disclosure. For persons having ordinary skills in the art, multiple variations and modifications may be made under the teachings of the present disclosure. For example, the assembly and/or function of the imaging system 100 may be varied or changed according to specific implementation scenarios. In some embodiments, the imaging system 100 may include one or more additional components and/or one or more components of the imaging system 100 described above may be omitted. Additionally or alternatively, two or more components of the imaging system 100 may be integrated into a single component. A component of the imaging system 100 may be implemented on two or more sub-components. In some embodiments, the gating system 170 may transmit the monitored ECG signal(s) to the processing device 140. The processing device 140 may cause the imaging device 110 to perform scan operations based on the received ECG signal(s).

Figure 2:
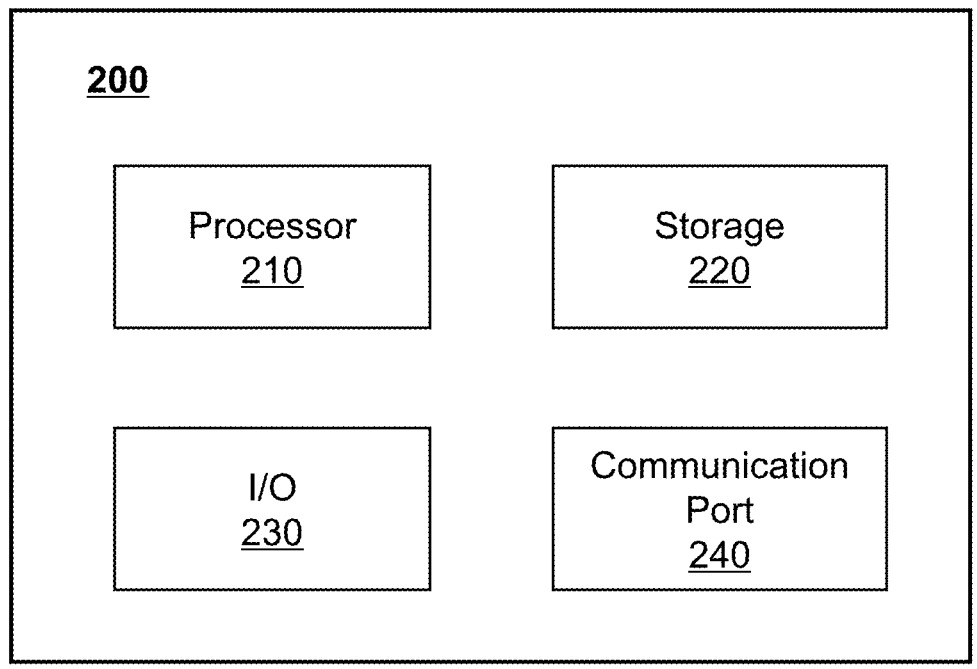
FIG. 2 is a schematic diagram illustrating hardware and/or software components of an exemplary computing device according to some embodiments of the present disclosure.

FIG. 2 is a schematic diagram illustrating hardware and/or software components of an exemplary computing device according to some embodiments of the present disclosure. In some embodiments, a component of the imaging system 100 (e.g., the processing device 140) may be implemented on the computing device 200. As illustrated in FIG. 2, the computing device 200 may include a processor 210, a storage 220, an input/output (I/O) 230, and a communication port 240.

The processor 210 may execute computer instructions (e.g., program codes) and perform functions of the processing device 140 in accordance with techniques described herein. The computer instructions may include, for example, routines, programs, objects, components, data structures, procedures, modules, and functions, which perform particular functions described herein. For example, the processor 210 may process scan data obtained from the imaging device 110, the terminal device 130, the storage device 150, and/or any other component of the imaging system 100. In some embodiments, the processor 210 may include one or more hardware processors, such as a microcontroller, a microprocessor, a reduced instruction set computer (RISC), an application-specific integrated circuit (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, and thus operations and/or method operations that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the imaging device 110, the terminal device 130, the storage device 150, and/or any other component of the imaging system 100. In some embodiments, the storage 220 may include a mass storage device, a removable storage device, a volatile read-and-write memory, a read-only memory (ROM), or the like, or any combination thereof. In some embodiments, the storage 220 may store one or more programs and/or instructions to perform exemplary methods described in the present disclosure. For example, the storage 220 may store a program (e.g., in the form of computer-executable instructions) for the processing device 140 to determine a gating signal for scanning a heart of a subject based on a plurality of channels of ECG signals.

The I/O 230 may input and/or output signals, data, information, etc. In some embodiments, the I/O 230 may enable a user interaction with the processing device 140. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing device 140 and the imaging device 110, the terminal device 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
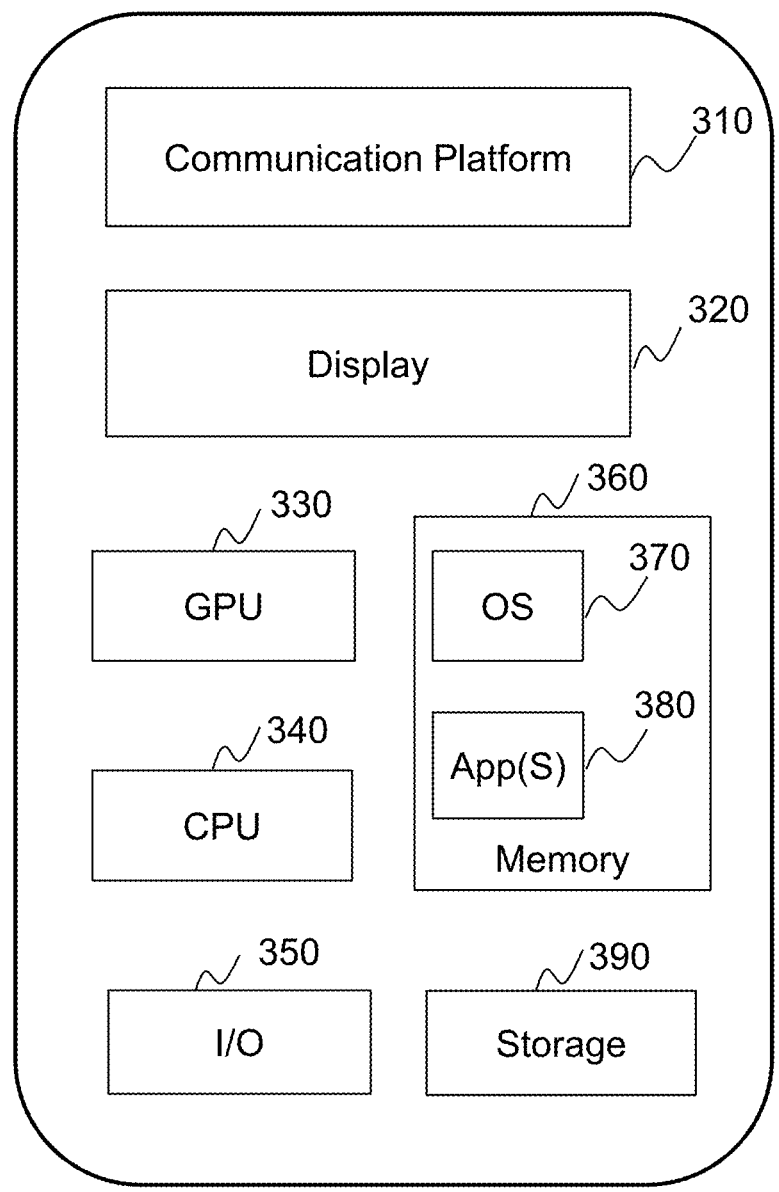
FIG. 3 is a schematic diagram illustrating exemplary hardware and/or software components of an exemplary mobile device according to some embodiments of the present disclosure.

FIG. 3 is a schematic diagram illustrating exemplary hardware components and/or software components of an exemplary mobile device according to some embodiments of the present disclosure. In some embodiments, one or more components (e.g., the terminal device 130 and/or the processing device 140) of the imaging system 100 may be implemented on the mobile device 300.

As illustrated in FIG. 3, the mobile device 300 may include a display 310, a communication platform 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the imaging system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4A:
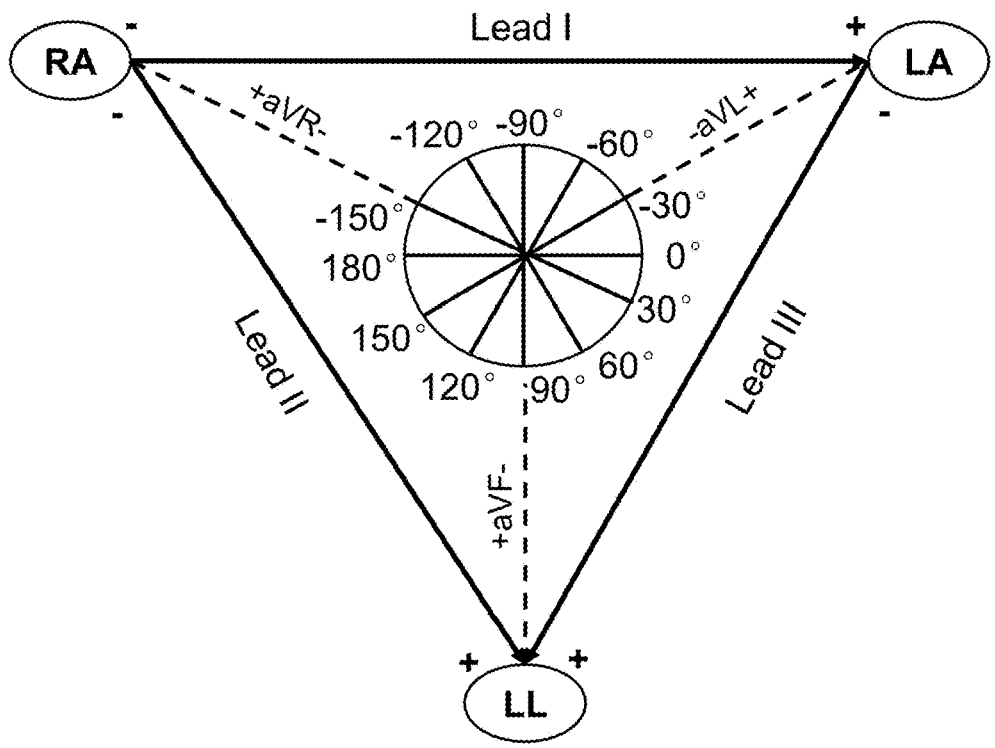
FIG. 4A is a schematic diagram illustrating a six-lead ECG acquisition system according to some embodiments of the present disclosure.

FIG. 4A is a schematic diagram illustrating a six-lead ECG acquisition system according to some embodiments of the present disclosure. According to FIG. 4A, the six-lead ECG acquisition system includes three electrodes and corresponding six leads including three bipolar limb leads (i.e., leads I, II, and III) and three augmented unipolar limb leads (i.e., leads aVR, aVL, and aVF). The three electrodes are positioned at a subject's right arm (RA), left arm (LA), and left leg (LL). Each pair of the three electrodes may form a bipolar limb lead that can describe the electrical activity of the heart of the subject from a particular angle. The three bipolar limb leads correspond to different angles in a clockwise polar coordinate system in which angle 0° is along lead I, and thus lead I is at 0°, lead II is at 60°, and lead III is at 120°.

Lead I is formed based on an electrical potential difference between electrode RA and electrode LA, and indicates the propagation of pulses from right to left of the subject. Lead II is formed based on an electrical potential difference between electrode RA and electrode LL, and indicates the propagation of pulses from superior to inferior (with minor influence on the pulse propagation from right to left). Lead III is formed based on an electrical potential difference between electrode LA and electrode LL, and indicates the propagation of pulses from superior to inferior (with minor influence on the pulse propagation from left to right). The three augmented unipolar limb leads are formed based on average measurements at the RA, the LA, and the LL. The lead aVR indicates the rightward propagation of pulses perpendicular to lead III. Lead aVL indicates the leftward propagation of pulses perpendicular to lead II. Lead aVF indicates the inferior-ward propagation of pulses perpendicular to lead I. The electrical potentials corresponding to any lead can be recorded as a channel of an ECG signal. A plurality of channels of ECG signals may provide spatial information associated with the heart's electrical activity.

In some embodiments, an ECG signal of a heart monitored by two electrodes in a changing magnetic field may have great noises generated by the changing magnetic field. For example, when the ECG signal is monitored in an MRI system, a gradient magnetic field corresponding to spatial coding may deteriorate the accuracy of the ECG signal monitored by the two electrodes. In some embodiments, in order to improve the accuracy of the monitored ECG signals, an electrode wire of at least one electrode may be winded to form at least two coils with different winding directions. More descriptions of the electrode wire may be found elsewhere of the present disclosure (e.g., FIGS. 13-16, and the descriptions thereof).

Figure 4B:
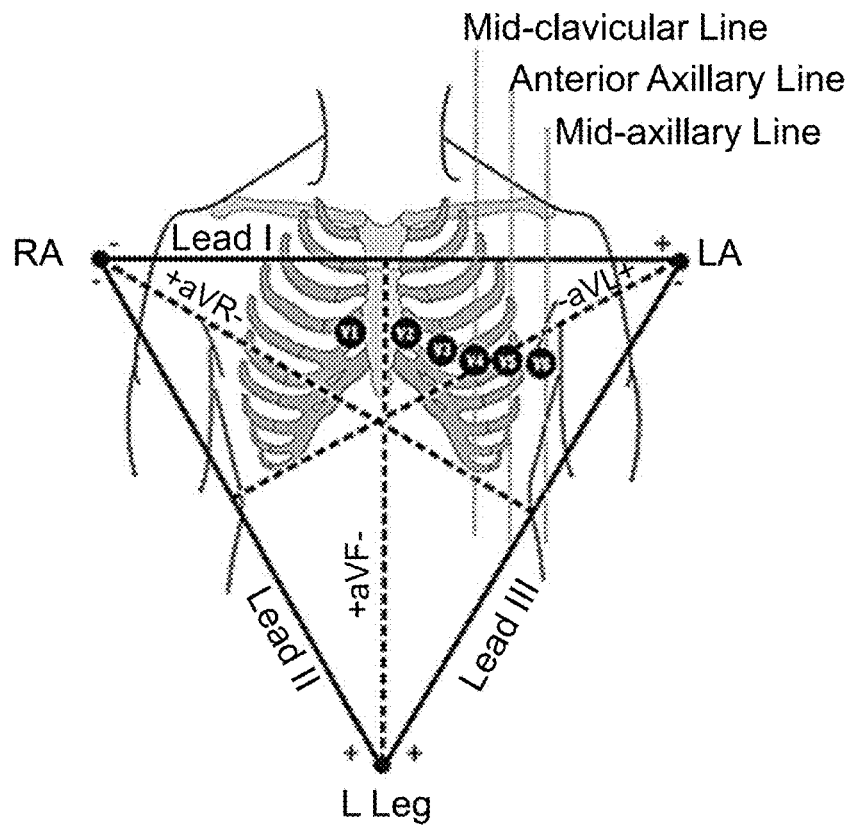
FIG. 4B is a schematic diagram illustrating a standard twelve-lead ECG acquisition system according to some embodiments of the present disclosure.

FIG. 4B is a schematic diagram illustrating a standard twelve-lead ECG acquisition system according to some embodiments of the present disclosure. As illustrated in FIG. 4B, the twelve leads includes three bipolar limb leads (i.e., leads I, II, and III), three augmented unipolar limb leads (i.e., leads aVR, aVL, and aVF), and six precordial leads (i.e., leads V1, V2, V3, V4, V5, and V6). Electrodes for the three bipolar limb leads and the three augmented unipolar limb leads are placed at a subject's right arm (RA), left arm (LA), and left leg (LL) as described in connection with FIG. 4A. Electrodes for the six precordial leads may be placed at six locations of the subject including the fourth intercostal space at the right sternum (V1), the fourth intercostal space at the left sternum (V2), the midway between placement of V2 and V4 (V3), the fifth intercostal space at the mid-clavicular line (V4), the anterior axillary line on a same horizontal level as V4 (V5), and the mid-axillary line on a same horizontal level as V4 and V5 (V6). The six precordial leads indicate pulse propagation through the heart in a cross-sectional (horizontal) plane. Leads V1, V2, and V3 indicate pulse propagation in the posterior to anterior direction, and negative changes of the leads V1, V2, and V3 ECG signals indicate pulse propagation in the opposite direction. Leads V4, V5, and V6 indicate pulse propagation in the lateral right to left direction, and negative changes of the leads V4, V5, and V6 ECG signals indicate pulse propagation in the opposite direction.

Figure 5A:
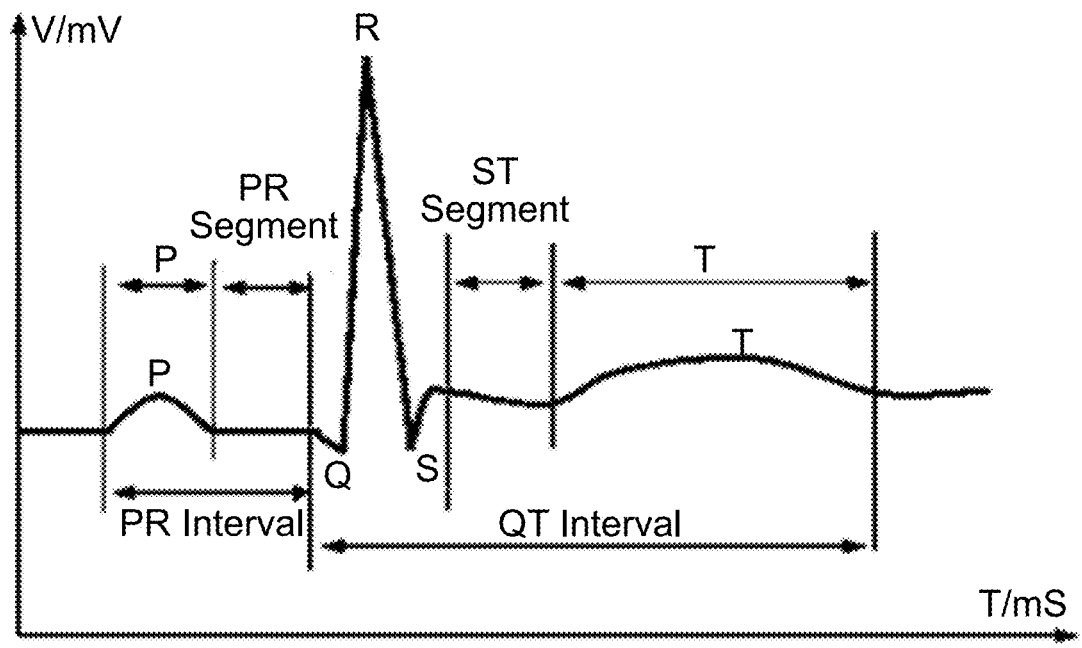
FIG. 5A is a schematic diagram illustrating an exemplary portion of an ECG signal indicating normal sinus rhythm of a human heart.

FIG. 5A is a schematic diagram illustrating an exemplary portion of an ECG signal indicating normal sinus rhythm of a human heart. The ECG may include a plurality of cycles. Generally, each cycle may include a P-wave, a QRS complex, and/or a T-wave, as shown in FIG. 5A. The QRS complex may include a Q-wave, an R-wave, and an S-wave. As shown in FIG. 5A, for each cycle of the ECG, a PR interval refers to a duration that extends from the beginning of the P-wave to the beginning of the QRS complex. A PR segment refers to a duration that extends from the end of the P-wave to the beginning of the QRS complex. A QT interval refers to a duration that extends from the beginning of the QRS complex to the end of the T-wave. An ST segment refers to a duration that extends from the end of the QRS complex to the beginning of the T-wave. For the ECG, the R-wave of the QRS complex may be the most significant wave among the components of one cycle of the ECG (e.g., the P-wave, the QRS complex, the T-wave). In some embodiments, the peak (of a wave (e.g., the P-wave, the Q-wave, the R-wave, or the S-wave)) may appear as an upward peak or a downward peak. As shown in FIG. 5A, the R-wave appears as an upward peak. In some embodiments, the ECG may be divided into a plurality of signal segments according to one or more cardiac cycles and the signal segments may be analyzed. A cardiac cycle may reflect the performance of the human heart from the beginning of one heartbeat to the end of the heartbeat (or the beginning of a next heartbeat). In some embodiments, the R-wave may be designated as a beginning and/or an end of a cardiac cycle. Accordingly, the cardiac cycle may refer to a duration between two adjacent R-waves. In this case, one cardiac cycle may be denoted as an R-R interval (or an R-R for short).

Figure 5B:
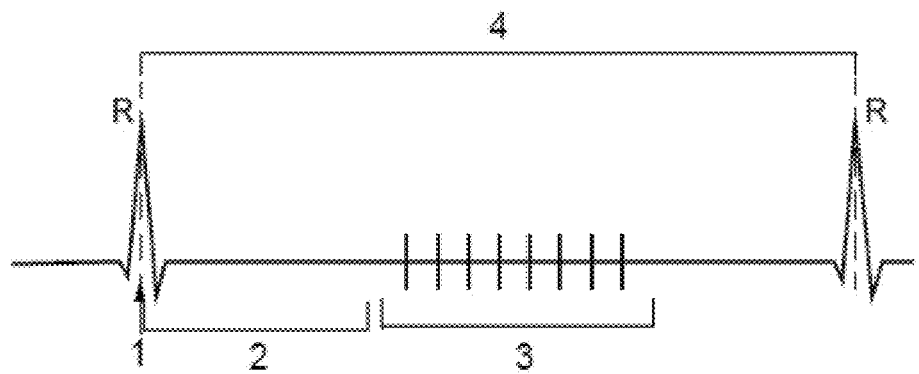
FIG. 5B is a schematic diagram illustrating an exemplary cardiac cycle of a subject according to some embodiments of the present disclosure.

FIG. 5B is a schematic diagram illustrating an exemplary cardiac cycle of a subject according to some embodiments of the present disclosure. In some embodiments, the imaging device 110 may be caused to perform a scan operation on the heart of the subject based on an ECG signal of the subject. The ECG signal may include a plurality of cardiac cycles as illustrated in FIG. 5B. It should be understood that because of the cardiac motion (e.g., the heartbeats) during the scan operation, cardiac images reconstructed based on scan data corresponding to different cardiac phases (e.g., corresponding different time periods in a cardiac cycle) may correspond to different areas of the heart. In some embodiments, a prospective gating mode or a retrospective gating mode may be used for the scan operation.

As used herein, the prospective gating mode may refer to a scanning process in which scan data acquisition only takes place in one or more selected time periods (or cardiac phases of one or more cardiac cycles). In some embodiments, a gating signal may be generated (e.g., by the gating system 170) based on the ECG signal, and the imaging device 110 may be gated by the gating signal. In some embodiments, the gating system 170 may transmit the gating signal to the controller 160, and the controller 160, after receiving the gating signal, may control the on and off of the imaging device 110 based on a gating delay and/or a gating width associated with the gating signal, so that the excitation source of the imaging device 110 (e.g., an X-ray tube of a CT device, or an ultrasound pulse source of an ultrasound device) may be only turned on after a first time period (of the gating delay) for a second time period (of the gating width), and the excitation source of the imaging device 110 may be turned off at other times (or the working voltage and/or working current of the excitation source may be maintained below an excitation threshold during the rest of one or more cardiac cycles). In some embodiments, the turning on or off of the excitation source of the imaging device 110 may refer to the opening or closing of one or more baffles corresponding to the excitation source (e.g., tungsten gate(s) of an X-ray source of a CT device). In other words, the excitation source may be always on, but scanning may be performed only when the baffle(s) are opened, and accordingly, scan data can be generated and acquired only when the baffle(s) are opened. As shown in FIG. 5B, an R-wave may be detected, and a cardiac cycle corresponding to an R-R interval 4 may be recognized. In response to the detection of the R-wave (i.e., starting point 1), a gating signal may be sent to the controller 160. After a trigger delay period (also referred to as a gating delay period) 2, the excitation source may be turned on to emit excitation beams (e.g., X-rays, ultrasound waves) for a scan data acquisition period (i.e., the time period 3) (also referred to as a gating width period). The scan data acquisition period may correspond to one or more certain cardiac phases of the heart. Thus, scan data of the heart generated under the prospective gating mode may correspond to the certain cardiac phase(s). Accordingly, a cardiac image generated based on the scan data may correspond to a certain cardiac phase of the heart.

The retrospective gating mode may refer to a scanning process in which scan data acquisition continuously takes place in all cardiac cycles during the scan operation. Under the retrospective gating mode, ECG signal acquisition may take place during the scan operation. After the scan data of the subject is acquired, target scan data corresponding to the time period 3 (or certain cardiac phases) of one or more cardiac cycles may be selected. Accordingly, cardiac image(s) reconstructed based on the target scan data may correspond to the certain cardiac phase(s) of the heart.

Figure 6A:
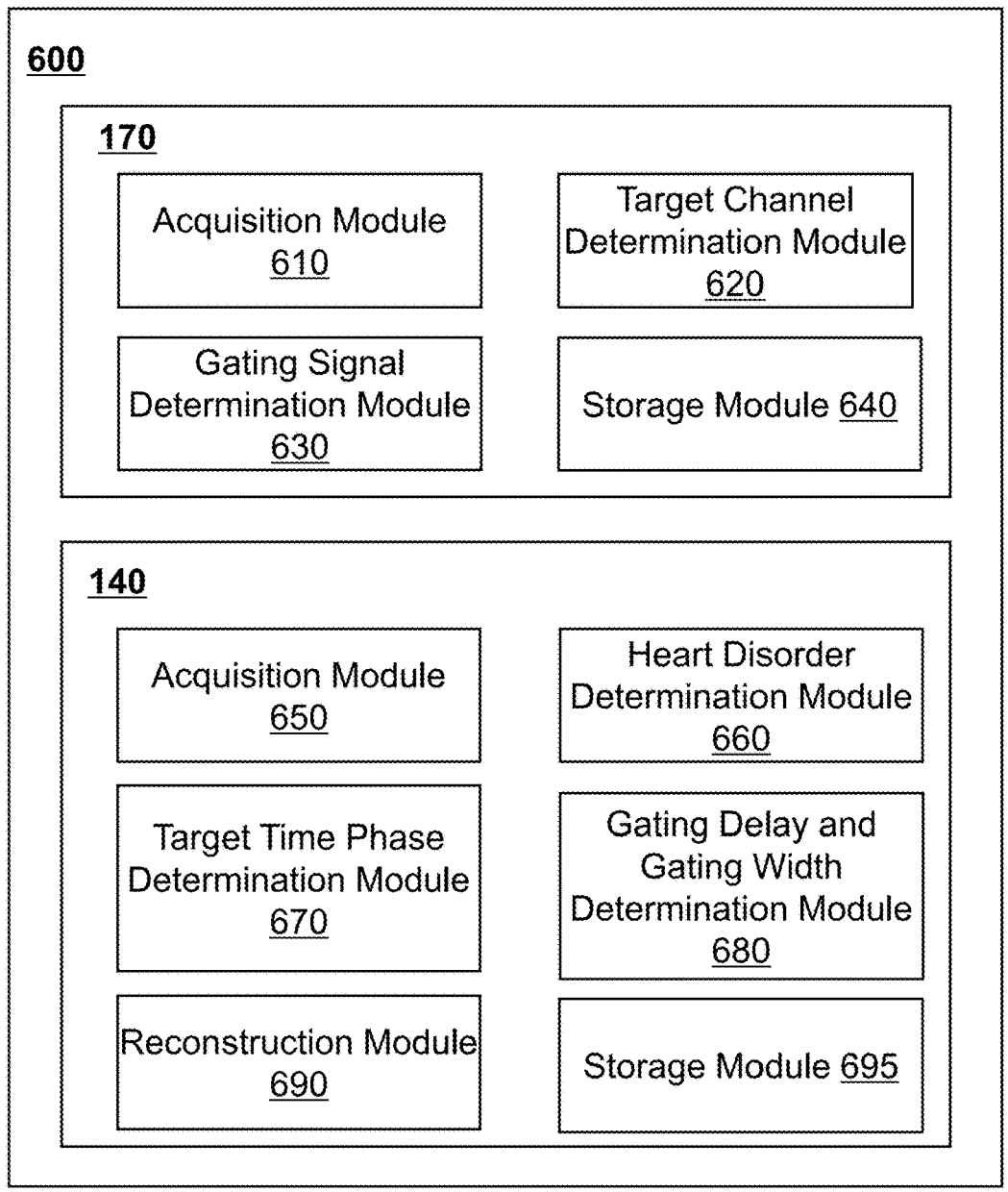
FIG. 6A is a block diagram illustrating an exemplary data processing system according to some embodiments of the present disclosure.

FIG. 6A is a block diagram illustrating an exemplary data processing system 600 according to some embodiments of the present disclosure. As illustrated in FIG. 6A, the data processing system 600 may include the gating system 170 and the processing device 140. The gating system 170 may include an acquisition module 610, a target channel determination module 620, a gating signal determination module 630, and a storage module 640. The processing device 140 may include an acquisition module 650, a heart disorder determination module 660, a target time phase determination module 670, a gating delay and gating width determination module 680, a reconstruction module 690, and a storage module 695. The modules may be hardware circuits of all or part of the data processing system 600. The modules may also be implemented as an application or set of instructions read and executed by the data processing system 600. Further, the modules may be any combination of the hardware circuits and the application/instructions.

The acquisition module 610 may be configured to obtain a plurality of channels of ECG signals of a heart of a subject. Each channel may correspond to a lead (such as, lead I, lead II, lead III, etc.). In some embodiments, the acquisition module 610 may preprocess the plurality of channels of ECG signals. For example, an amplifying until of the acquisition module 610 may amplify the corresponding channel of ECG signal. As another example, a filtering unit of the acquisition module 610 may filter the corresponding amplified ECG signal. In some embodiments, the acquisition module 610 may be used to obtain second ECG signals from the plurality of channels monitored during the scan operation.

The target channel determination module 620 may be configured to identify a target channel of ECG signal from the plurality of channels of ECG signals. An amplitude of a characteristic wave of the target channel of ECG signal may be the maximum amplitude among amplitudes of corresponding characteristic waves of the plurality of channels of ECG signals. In some embodiments, the target channel determination module 620 may determine an updated target channel of ECG signal based on the plurality of channels of second ECG signals monitored during the scan operation. The target channel determination module 620 may switch from the target channel to the updated target channel for ECG signal monitoring and/or analyzing.

The gating signal determination module 630 may be configured to generate a gating signal based on the target channel of ECG signal. The gating system 170 may detect the characteristic wave of the current cardiac cycle based on the target channel of ECG signal. In response to the detection of the characteristic wave of the current cardiac cycle of the target channel of ECG signal, the gating signal determination module 630 may generate the gating signal, and transmit the gating signal to the controller 160. In some embodiments, the gating signal determination module 630 may generate the gating signal based on the updated target channel of second ECG signal obtained during the scan operation.

The storage module 640 may be configured to store data and/or instructions associated with the gating system 170. For example, the storage module 640 may store the plurality of channels of ECG signals, the target channel of ECG signal monitored during the scan operation, the plurality of channels of second ECG signals, etc. In some embodiments, the storage module 640 may be same as the storage device 150 and/or the storage 220 in configuration.

The acquisition module 650 may be configured to obtain data and/or information from the gating system 170 and/or the imaging device 110. For example, the acquisition module 650 may obtain scan data generated by scanning the heart of the subject using the imaging device 110. As another example, the acquisition module 650 may obtain the target channel of ECG signal of the subject that are monitored during the scanning of the heart from the gating system 170. In some embodiments, the acquisition module 650 may be same as the acquisition module 610 in configuration.

The heart disorder determination 660 may be configured to determine a heart disorder of the heart based at least in part on the plurality of channels of ECG signals. For example, the heart disorder determination 660 may determine one or more features of the plurality of channels of ECG signals. The heart disorder determination 660 may determine the heart disorder of the heart based at least in part on the one or more features. In some embodiments, the heart disorder determination 660 may update the heart disorder based at least in part on the second ECG signals.

The target time phase determination module 670 may be configured to determine a target time phase based on the heart disorder of the heart. In some embodiments, the target time phase determination module 670 may update the target time phase based on the updated heart disorder of the heart determined based on the second ECG signals (from the plurality of channels) monitored during the scan operation.

The gating delay and gating width determination module 680 may be configured to determine a gating delay and a gating width based on the target time phase. In some embodiments, under the retrospective gating mode, the gating delay and gating width determination module 680 may determine the gating delay and the gating width of the current cardiac cycle based on a duration of a previous cardiac cycle. In some embodiments, the gating delay and gating width determination module 680 may determine the gating delay and the gating width of the current cardiac cycle based on a plurality of durations corresponding to a plurality of cardiac cycles previous to the current cardiac cycle. The gating delay and gating width determination module 680 may transmit the gating delay and the gating width to the controller 160 for controlling the imaging device 110.

The reconstruction module 680 may be configured to reconstruct a cardiac image based on the scan data and/or the target channel of ECG signal. In some embodiments, the reconstruction module 680 may directly reconstruct the cardiac image based on the target scan data. In some embodiments, the reconstruction module 680 may determine target scan data from the scan data based on the target channel of ECG signal. The target scan data may include scan data corresponding to the target time phase associated with the target channel of ECG signal. The reconstruction module 680 may reconstruct the cardiac image based on the target scan data.

The storage module 695 may be configured to store data and/or instructions associated with the processing device 140. For example, the storage module 695 may store the plurality of channels of ECG signals, the plurality of channels of second ECG signals, the scan data of the subject, the target scan data of the subject, etc. In some embodiments, the storage module 695 may be same as the storage device 150 and/or the storage module 610 in configuration.

Figure 6B:
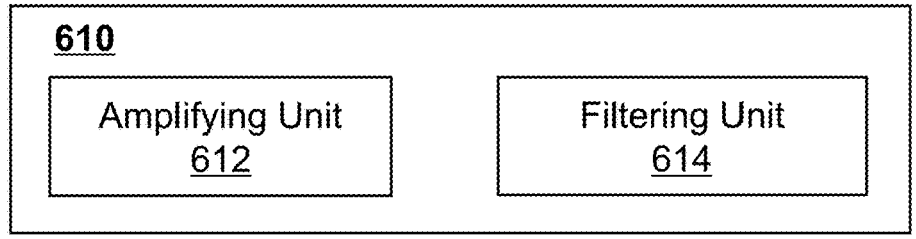
FIG. 6B is a block diagram illustrating an exemplary acquisition module of a gating system according to some embodiments of the present disclosure.

FIG. 6B is a block diagram illustrating an exemplary acquisition module of a gating system according to some embodiments of the present disclosure. As illustrated in FIG. 6B, the acquisition module 610 may include one or more amplifying units 612 and one or more filtering units 614.

The one or more amplifying units 612 may be configured to amplify a plurality of channels of ECG signals. Each amplifying unit 612 may correspond to one channel.

The one or more filtering units 614 may be configured to filter the amplified ECG signals. Each filtering unit 614 may correspond to one amplifying unit 612.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, a module mentioned above may be divided into two or more units. For example, the gating signal determination module 630 may be divided into two units, one of which may be configured to determine the gating signal, and the other one may be configured to cause the imaging device 110 to perform the scan operation on the heart based on the gating signal. In some embodiments, the data processing system 600 may include one or more additional modules. For example, the data processing system 600 may further include a transmission module (not shown in FIG. 6A).

Figure 7:
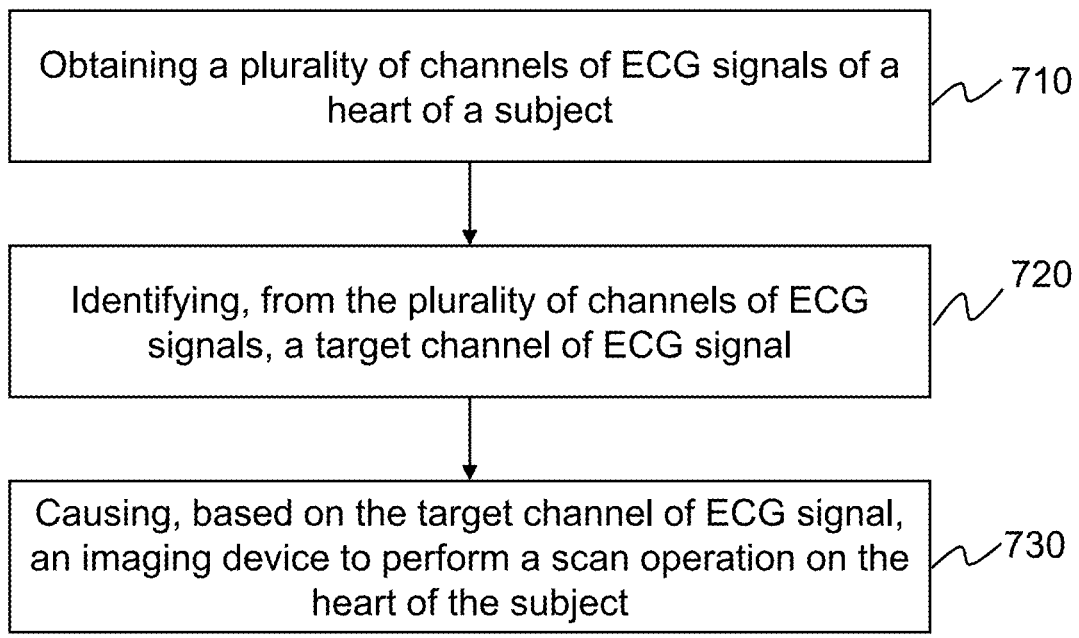
FIG. 7 is a flowchart illustrating an exemplary process for causing an imaging device to perform a scan operation on a heart of a subject according to some embodiments of the present disclosure.

FIG. 7 is a flowchart illustrating an exemplary process for causing an imaging device to perform a scan operation on a heart of a subject according to some embodiments of the present disclosure. At least a portion of process 700 may be implemented on the computing device 200 as illustrated in FIG. 2 or the mobile device 300 as illustrated in FIG. 3. In some embodiments, one or more operations of process 700 may be implemented in the imaging system 100 as illustrated in FIG. 1. For example, a portion of process 700 may be stored in the storage module 640 of the gating system 170 in the form of instructions, and invoked and/or executed by the gating system 170. As another example, another portion of process 700 may be stored in the storage module 695 of the processing device 140 in the form of instructions, and invoked and/or executed by the processing device 140. The operations of the illustrated process presented below are intended to be illustrative. In some embodiments, the process 700 may be accomplished with one or more additional operations not described, and/or without one or more of the operations discussed. Additionally, the order of the operations of the process 700 illustrated in FIG. 7 and described below is not intended to be limiting.

In 710, the gating system 170 (e.g., the acquisition module 610) may obtain a plurality of channels of electrocardiogram (ECG) signals of a heart of a subject. The subject may include a patient or an animal. In some embodiments, the heart of the subject may be an artificial heart. In some embodiments, the plurality of channels may correspond to multiple leads (such as, lead I, lead II, lead III, etc.) as described in FIGS. 4A and 4B. Each channel of ECG signal may correspond to a plurality of cardiac cycles of the heart. Each cardiac cycle may include a P-wave, a QRS complex (including an R-wave, a Q-wave, and an S-wave), a T-wave, etc., as described in FIGS. 5A and 5B.

Figure 10A:
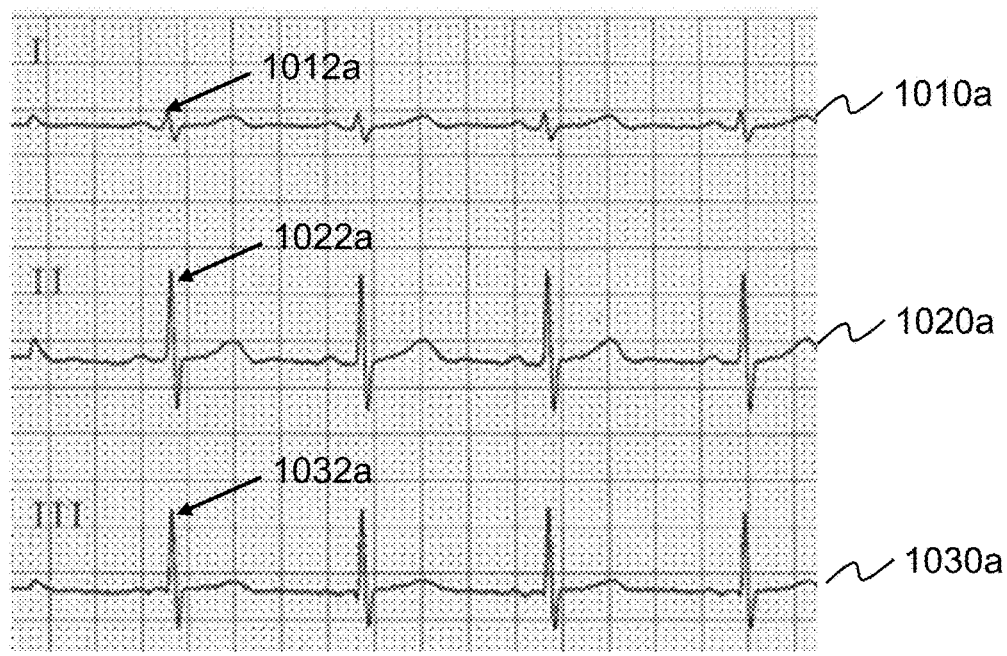
FIG. 10A illustrates exemplary ECG signals corresponding to leads I, II, and III of a healthy human heart according to some embodiments of the present disclosure.

In some embodiments, the gating system 170 may obtain the plurality of channels of ECG signals from a storage medium (e.g., the storage device 150, and/or the storage module 640) of the imaging system 100. For example, an ECG signal detector (e.g., a multi-lead sensing device) may be used to obtain the plurality of channels of ECG signals, and the obtained ECG signals may be stored in the storage device 150. The gating system 170 may obtain the plurality of channels of ECG signals from the storage device 150. In some embodiments, the ECG signal detector may be integrated into the gating system 170. The gating system 170 may obtain the plurality of channels of ECG signals from the ECG signal detector directly. For example, the gating system 170 may obtain the plurality of channels of ECG signals in real time, substantially real time, or periodically. In some embodiments, the ECG signal detector may be integrated in the imaging device 110. The ECG signal detector integrated in the imaging device 110 may monitor the plurality of channels of ECG signals in real time when the subject is placed on the table 114, and send the monitored ECG signals to the gating system 170. In some embodiments, the ECG signal detector may include one or more sensors (e.g., electrodes), one or more amplifying circuits, one or more filtering circuits, or the like, or any combination thereof. In some embodiments, each of the plurality of channels of ECG signals may be a digital ECG signal. The ECG signal may include a plurality of samples. In some embodiments, the ECG signal detector may collect the samples in a predetermined sampling rate in real time. The plurality of samples may form an ECG signal including one or more cycles, as illustrated in FIGS. 5B and 10A.

In some embodiments, the plurality of channels of ECG signals may be preprocessed ECG signals. For example, the plurality of channels of ECG signals may be ECG signals that are filtered and/or amplified by the ECG signal detector. As another example, the plurality of channels of ECG signals may be preprocessed by the gating system 170. Specifically, in some embodiments, the gating system 170 may perform a preprocessing operation on each of the plurality of channels of ECG signals. The preprocessing operation may include an amplifying operation, a filtering operation, a denoising operation, or the like, or any combination thereof.

It should be understood that the frequency of an ECG signal of a human heart is mainly in a range of 0.05 Hz to 100 Hz, the amplitude of an ECG signal of a human heart is in a range of 0 to 4 mV, and the impedance of ECG electrodes is relatively large (generally more than several hundred kilo ohms), and thus, the ECG signal of a human heart may be generally weak. In such cases, the gating system 170 (e.g., the amplifying units 612 illustrated in FIG. 6B) may perform the amplifying operation on the plurality of channels of ECG signals to improve signal quality. In some embodiments, the gating system 170 may perform the amplifying operation based on a gain amplifier, an operational amplifier, an operational amplifier circuit, or any other device or circuit having a signal amplifying function.

In some embodiments, the plurality of channels of ECG signals may be mixed with other bioelectric signals (e.g., electromyography, EMG) which can cause background noise in the ECG signals. In such cases, the gating system 170 (e.g., the filtering unit 614s illustrated in FIG. 6B) may perform the filtering operation on the plurality of channels of ECG signals to increase the signal-to-noise ratio (SNR). In some embodiments, the filtering operation may be performed based on a band stop filter, a power frequency notch circuit, a high-pass filter, a high-pass filter circuit, a low-pass filter, a low-pass filter circuit, or the like, or any combination thereof. As used herein, the band stop filter and/or the power frequency notch circuit may be used to selectively decrease the noise generated by the power frequency (e.g., 50 Hz or 60 Hz) interference. The high-pass filter and/or the high-pass filter circuit may be used to filter out a signal whose frequency is less than a first threshold frequency (e.g., 10 Hz), and retain a signal whose frequency is greater than the first threshold frequency. The low-pass filter and/or the low-pass filter circuit may be used to filter out a signal whose frequency is greater than a second threshold frequency (e.g., a cut-off frequency, 100 Hz), and retain a signal whose frequency is less than the second threshold frequency. It should be noted that the filtering of the ECG signals aims at reducing or avoiding high-frequency and/or low-frequency noises of the plurality of channels of ECG signals. In some embodiments, the gating system 170 may preprocess the plurality of channels of ECG signals in real time or substantially real time.

In 720, the gating system 170 (e.g., the target channel determination module 620) may identify a target channel of ECG signal from the plurality of channels of ECG signals. In some embodiments, an amplitude of a characteristic wave of the target channel of ECG signal may be the maximum amplitude among amplitudes of corresponding characteristic waves of the plurality of channels of ECG signals. It should be noted that a wave with a relatively high amplitude may be identified easily and accurately. Thus, by using the target channel of ECG signal having the characteristic wave with the maximum amplitude among amplitudes of corresponding characteristic waves of the plurality of channels of ECG signals to gate the scan operation performed on the heart, a failure of the scan operation may be avoided, especially when a predetermined channel of ECG signal is unavailable (e.g., the characteristic wave of the predetermined channel of ECG signal is unidentified), and thus, the scanning and/or reconstruction accuracy can be improved.

In some embodiments, the target channel may be varied in different cardiac cycles. For example, the target channels corresponding to two adjacent cardiac cycles of a subject suffering from arrhythmia may be different. A first cardiac cycle may correspond to a first target channel (e.g., Lead II), while a second cardiac cycle may correspond to a second target channel (e.g., Lead III).

As used herein, a characteristic wave may refer to a wave of the ECG signals (e.g., the P-wave, the Q-wave, the R-wave, the S-wave, or the T-wave) that has a relatively significant peak, is easy to identify, and/or can be used to gate an imaging device to perform a scan operation on the heart of the subject. In some embodiments, a time period between two adjacent characteristic waves may correspond to a scanning cycle. An amplitude of a wave may refer to the amplitude of the peak of the wave. In some embodiments, the characteristic wave may be set according to a default setting of the imaging system 100 or preset by a user or operator via the terminal device 130. For example, the characteristic wave may be predetermined as the Q-wave according to a default of the imaging system 100. As another example, a user (e.g., a doctor) may set the R-wave as the characteristic wave via the terminal device 130. In some embodiments, the gating system 170 may determine an amplitude of the characteristic wave in one or more cardiac cycles (e.g., each cardiac cycle) of each channel of ECG signal. The gating system 170 may compare the amplitudes of the characteristic waves of the plurality of channels of ECG signals and determine the target channel of ECG signal.

Figure 10B:
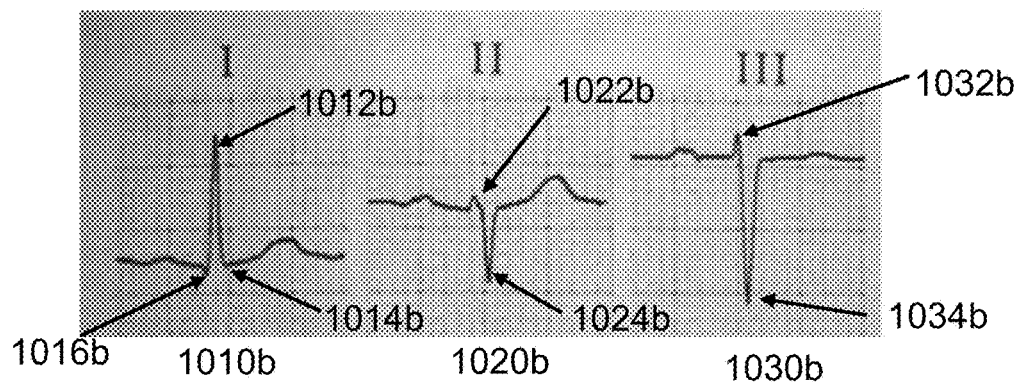
FIG. 10B illustrates exemplary ECG signals corresponding to leads I, II, and III of a first abnormal human heart according to some embodiments of the present disclosure.

In some embodiments, the gating system 170 may determine an amplitude of each wave in a cardiac cycle (or the QRS complex of a cardiac cycle) of each channel of ECG signal. In some embodiments, the gating system 170 may compare the amplitudes of all the waves of the plurality of channels of ECG signals, and designate the wave having the maximum amplitude as the characteristic wave. The gating system 170 may designate the channel of ECG signal having the wave with the maximum amplitude as the target channel of ECG signal. For example, for three channels of ECG signals 1010b, 1020b, and 1030b as illustrated in FIG. 10B, the ECG signal 1010b may correspond to lead I, the ECG signal 1020b may correspond to lead II, and the ECG signal 1030b may correspond to lead III. The gating system 170 may determine the amplitudes of a Q-wave, an R-wave, and an S-wave of the ECG signal 1010b, the amplitudes of a Q-wave, an R-wave, and an S-wave of the ECG signal 1020b, and the amplitudes of a Q-wave, an R-wave, and an S-wave of the ECG signal 1030b. The gating system 170 may designate a wave (e.g., the S-wave) having the maximum amplitude among the three Q waves, three R waves, and three S waves as the characteristic wave. The gating system 170 may designate the ECG signal 1030b corresponding to lead III as the target channel of ECG signal. In some embodiments, the gating system 170 may specify a reference channel. The gating system 170 may determine the characteristic wave based on the reference channel of ECG signal. For example, the gating system 170 may designate the wave with the maximum amplitude in the reference channel of ECG signal as the characteristic wave.

In some embodiments, the gating system 170 may identify each wave on each channel of ECG signal based on a wave identification operation. In some embodiments, the wave identification operation may be performed using a threshold detection algorithm, a wavelet transform algorithm, a machine learning model, or the like, or any combination thereof.

In 730, the controller 160 may cause an imaging device (e.g., the imaging device 110) to perform a scan operation on the heart of the subject. In some embodiments, operation 730 may be performed based on the target channel of ECG signal monitored during the scan operation.

In some embodiments, the scan operation may be performed under a prospective gating mode or a retrospective gating mode. When using the prospective gating mode, the gating system 170 may generate a gating signal based on the target channel of ECG signal monitored during the scan operation. The gating system 170 may send the gating signal to the controller 160, and the controller 160, after receiving the gating signal, may trigger the imaging device to scan the heart based on the gating signal. More descriptions regarding scan operation under the prospective gating mode may be found elsewhere in the present disclosure (e.g., FIG. 8 and the descriptions thereof).

In some embodiments, under the retrospective gating mode, the controller 160 may control the imaging device 110 to generate or collect scan data during the scan operation. The gating system 170 may obtain a target ECG signal from the target channel monitored during the scan operation, and transmit the monitored target ECG signal (obtained from the target channel) to the processing device 140. For example, the gating system 170 may monitor the target ECG signal in real time or substantially real time during the scan operation and store the target ECG signal in the storage module 640. The generation or collection of the scan data by the imaging device 110 and the monitoring of the target ECG signal by the gating system 170 may be performed (substantially)

simultaneously. After the scan operation is performed, the gating system 170 may transmit the target ECG signal to the processing device 140, and the imaging device 110 may transmit the scan data to the processing device 140. The processing device 140 may reconstruct one or more cardiac images of the heart based on the scan data and the target ECG signal of the target channel. For example, the processing device 140 may automatically select target scan data from the scan data based on the target ECG signal (e.g., a predetermined time phase associated with the target ECG signal). The processing device 140 may reconstruct the cardiac image(s) of the heart based on the target scan data. As another example, the processing device 140 may recommend a time phase (e.g., the predetermined time phase or a default setting time phase of the imaging system 100) to a user (e.g., a doctor), and the user may select and/or determine a target time phase. The processing device 140 may reconstruct a cardiac image of the heart based on the scan data and the target time phase. In such cases, when reconstructing a cardiac image of the heart, a user (e.g., a doctor) may easily select target scan data from scan data generated during the scan operation based on the target channel of ECG signal, thereby reducing the reconstruction time and improving image reconstruction efficiency and accuracy.

In some embodiments, the processing device 140 may determine a heart disorder of the heart based at least in part on the ECG signals obtained in 710. The processing device 140 may determine a target time phase based on the heart disorder of the heart. The processing device 140 may determine, from the scan data, target scan data corresponding to the target time phase of the target channel of ECG signal. The processing device 140 may reconstruct the cardiac image based on the target scan data. In some embodiments, the gating system 170 may obtain second ECG signals from the plurality of channels monitored during the scan operation. The gating system 170 may determine an updated target channel of ECG signal based on the plurality of channels of second ECG signals. The gating system 170 may transmit the second ECG signals and/or the updated target channel of ECG signal to the processing device 140. The processing device 140 may reconstruct cardiac image(s) of the heart based on the scan data and the updated target channel of ECG signal. For example, the processing device 140 may determine target time phase(s) of the updated target channel of ECG signal, and reconstruct cardiac image(s) based on the scan data corresponding to the target time phase(s). In some embodiments, in response to updating the target channel of ECG signal, the processing device 140 may prompt a user that the target channel of ECG signal is updated. In some embodiments, the processing device 140 may determine an updated heart disorder of the heart based at least in part on the second ECG signals. The processing device 140 may update the target time phase based on the updated heart disorder of the heart. The processing device 140 may determine, from the scan data, updated target scan data corresponding to the updated target time phase of the target channel of ECG signal. The processing device 140 may reconstruct the cardiac image(s) based on the updated target scan data. More descriptions regarding the reconstruction of cardiac image(s) based on the scan data and the ECG signal of the target channel may be found as described in connection with operation 940 in FIG. 9.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the process 700 may include an additional operation to reconstruct a cardiac image of the heart based on scan data generated during the scan operation. As another example, the process 700 may further include an additional operation to transmit the cardiac image to a terminal device (e.g., a terminal device 130) for display.

Figure 8:
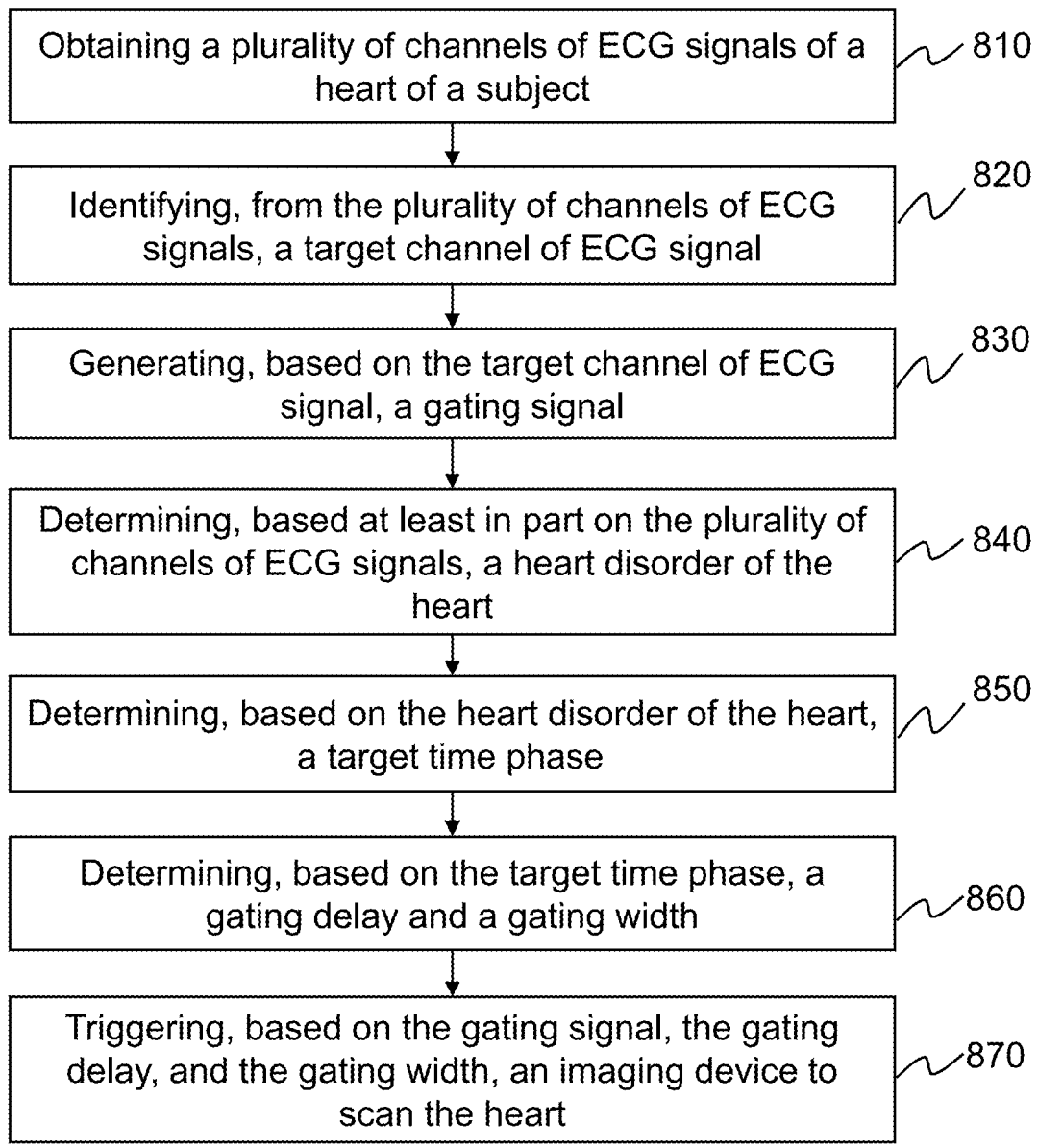
FIG. 8 is a flowchart illustrating an exemplary process for triggering an imaging device to scan a heart according to some embodiments of the present disclosure.

FIG. 8 is a flowchart illustrating an exemplary process for triggering an imaging device to scan a heart according to some embodiments of the present disclosure. At least a portion of process 800 may be implemented on the computing device 200 as illustrated in FIG. 2 or the mobile device 300 as illustrated in FIG. 3. In some embodiments, one or more operations of process 800 may be implemented in the imaging system 100 as illustrated in FIG. 1. For example, a portion of process 800 may be stored in the storage module 640 of the gating system 170 in the form of instructions, and invoked and/or executed by the gating system 170. As another example, another portion of process 800 may be stored in the storage module 695 of the processing device 140 in the form of instructions, and invoked and/or executed by the processing device 140. The operations of the illustrated process presented below are intended to be illustrative. In some embodiments, the process 800 may be accomplished with one or more additional operations not described, and/or without one or more of the operations discussed. Additionally, the order of the operations of the process 800 illustrated in FIG. 8 and described below is not intended to be limiting. The process 800 may be associated with a scan operation under a prospective gating mode. ECG signal(s) may be detected and/or used during the scan operation. Because the cardiac motion associated with contraction and relaxation of a heart normally has periodicity synchronous with the ECG signal(s), a scanning cycle associated with the cardiac motion may correspond to one ECG cycle. In some embodiments, the term "scanning cycle" and "cardiac cycle" are used interchangeably in the present disclosure.

In 810, the gating system 170 (e.g., the acquisition module 610) may obtain a plurality of channels of electrocardiogram (ECG) signals of a heart of a subject.

In some embodiments, the plurality of channels of ECG signals of the heart may be monitored before the scan operation is performed. For example, when the subject is placed on the table 114, an ECG signal detector may monitor the plurality of channels of ECG signals and/or store the monitored ECG signals in the storage device 150. The gating system 170 may obtain the plurality of channels of ECG signals from the storage device 150. In some embodiments, the plurality of channels of ECG signals may be monitored during the scan operation. For example, the current scanning cycle may be performed after one or more scanning cycles in the scan operation, and the plurality of channels of ECG signals may be ECG signals monitored during the one or more scanning cycles. The gating system 170 may transmit the monitored ECG signal(s) to the processing device 140 for further processing (e.g., determining a heart disorder as described in operation 840).

In 820, the gating system 170 (e.g., the target channel determination module 620) may identify a target channel of ECG signal from the plurality of channels of ECG signals. In some embodiments, the amplitude of a characteristic wave of the target channel of ECG signal may be the maximum amplitude among amplitudes of corresponding characteristic waves of the plurality of channels of ECG signals. Operation 820 may be similar to operation 720 of process 700 described above, the descriptions of which may be found in the present disclosure in connection with FIG. 7.

In some embodiments, the gating system 170 may determine an updated target channel of ECG signal based on second ECG signals from the plurality of channels. For example, if the heart is under an abnormal condition, one or more characteristic waves of the target channel of ECG signal may become unidentifiable, and accordingly, the gating system 170 may switch from the target channel (e.g., lead II) to an updated target channel (e.g., lead I) for ECG signal monitoring and/or analyzing. Accordingly, the gating system 170 may cause the imaging device to perform the scan operation on the heart based on the updated target channel of ECG signal. For example, the gating system 170 may obtain the second ECG signals of the plurality of channels monitored during the scan operation. For one or more previous cardiac cycles, if one or more characteristic waves of the target channel of ECG signal during the previous cardiac cycle(s) are unidentified, the gating system 170 may identify a target channel (i.e., the updated target channel) of ECG signal from the plurality of channels of second ECG signals. The gating system 170 140 may automatically switch the target channel to the updated target channel that is useable. That is, the second ECG signal from the updated target channel may be used to gate the imaging device. In some embodiments, in response to determining that the target channel is updated, the processing device 140 may prompt a user that the target channel of ECG signal is updated (or switched to another channel). In some embodiments, the processing device 140 may just display the updated target channel of ECG signal to the user.

In 830, the gating system 170 (e.g., the gating signal determination module 630) may generate a gating signal based on the target channel of ECG signal obtained in 810. In some embodiments, the gating system 170 may generate the gating signal based on the updated target channel of second ECG signal obtained during the scan operation.

The gating signal may be an instruction for triggering an excitation source of an imaging device (e.g., an X-ray tube of a CT device) to emit radioactive rays to scan the heart. In some embodiments, a starting time point of the current scanning cycle (e.g., a starting time point for the emission of the radioactive rays) may be determined based on the gating signal. The gating system 170 may detect the characteristic wave of the current cardiac cycle based on the target channel of ECG signal. In response to the detection of the characteristic wave of the current cardiac cycle of the target channel of ECG signal, the gating system 170 may generate the gating signal, and transmit the gating signal to the controller 160.

In 840, the processing device 140 (e.g., the heart disorder determination module 660) may determine a heart disorder of the heart based at least in part on the plurality of channels of ECG signals.

The processing device 140 may determine one or more features of the plurality of channels of ECG signals. The processing device 140 may determine the heart disorder of the heart based at least in part on the one or more features. For example, the processing device 140 may query a library including a relationship between the one or more features and one or more heart disorders based on the one or more features. The processing device 140 may determine the heart disorder of the heart based on the query result. As another example, the processing device 140 may determine the heart disorder based on a heart disorder identification model. The heart disorder identification model may be trained based on a plurality of groups of training data. Each group of training data may include one or more features of a sample ECG signal and a corresponding heart disorder associated with the sample ECG signal. The processing device 140 may input the one or more features of the ECG signals into the heart disorder identification model to determine the heart disorder of the heart. In some embodiments, the one or more features of the plurality of channels of ECG signals may include a position of each wave (e.g., the Q-wave, the R-wave, the S-wave, the P-wave, etc.) of each channel of ECG signal, an amplitude of each wave of each channel of ECG signal, a peak width of each wave of each channel of ECG signal, a width of a QRS complex of each channel of ECG signal, a deflection direction of a QRS axis of the heart, comparison results between the plurality of channels of ECG signals of the heart and corresponding ECG signals of a healthy heart, or the like, or any combination thereof. For example, according to ECG signals in FIGS. 10A and 10B, one or more features of ECG signals of a first subject corresponding to FIG. 10B may include: (1) the QRS complexes of both the ECG signal 1020*b* of lead II and the ECG signal 1030*b* of lead III represent an rS pattern (e.g., a relatively small positive wave (r), and followed by a relatively large negative wave (S)); (2) the amplitude of S-wave 1034*b* of lead III is greater than the amplitude of S-wave 1024*b* of lead II; (3) the QRS complex of the ECG signal 1010*b* of lead I represents a qR pattern (e.g., a relatively small negative wave (q) and followed by a relatively large positive wave (R)); and (4) the QRS axis (or mean QRS axis) is leftward. Accordingly, a heart disorder of the first heart of the first subject may be determined as a disease relating to the left anterior descending artery (LAD). As another example, according to ECG signals in FIGS. 10A and 10C, one or more features of ECG signals of a second subject corresponding to FIG. 10C may include: (1) the width of S-wave 1014*c* of lead I is increased (e.g., greater than 0.04 seconds); and (2) the QRS complexes of the three ECG signals 1010*c*, 1020*c*, and 1030*c* lasts more than 0.12 seconds. Accordingly, a heart disorder of the second heart of the second subject may be determined as a disease relating to the right anterior descending artery.

In some embodiments, the gating system 170 may obtain, from the plurality of channels, second ECG signals monitored during the scan operation and transmit them to the processing device 140. The processing device 140 may update the heart disorder based at least in part on the second ECG signals.

In 850, the processing device 140 (e.g., the target time phase determination module 670) may determine a target time phase based on the heart disorder of the heart.

As used herein, a time phase refers to a phase of an ECG signal (e.g., the target channel of ECG signal) (or a time period or a time point in each cardiac cycle associated with the ECG signal). The target time phase may refer to a time phase at which the cardiac motion amplitude of the heart is relatively small or the movement of the heart (or a structure of the heart) is relatively slow (e.g., the slowest). A cardiac cycle may correspond to a time period between two adjacent characteristic waves of the target channel of ECG signal. For illustration purposes, an R-wave may be taken as an example of the characteristic wave. Thus, the duration of a cardiac cycle may be the time interval between two adjacent R-waves, i.e., an R-R interval (or an R-R for short). The target time phase may be denoted by a percentage of the duration of the cardiac cycle.

Figure 10C:
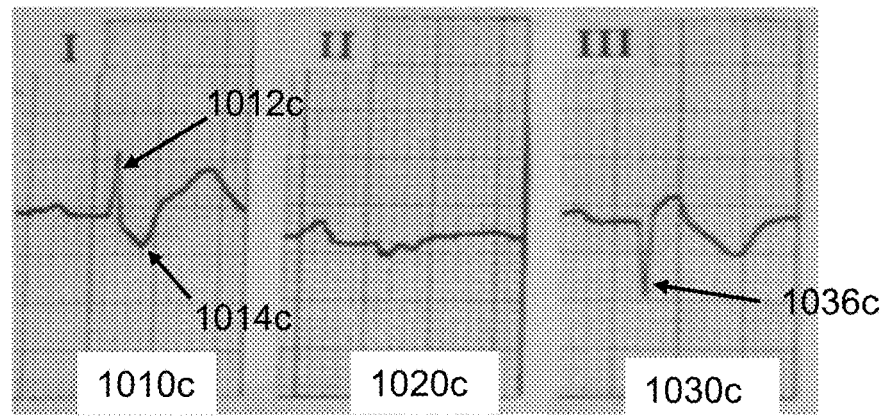
FIG. 10C illustrates exemplary ECG signals corresponding to leads I, II, and III of a second abnormal human heart according to some embodiments of the present disclosure.

In some embodiments, the processing device 140 may query a library (e.g., Table 1 illustrated in FIGS. 10A-10C)

including a relationship between one or more heart disorders and one or more target time phases based on the heart disorder of the heart. The processing device 140 may determine the target time phase based on the query result. In some embodiments, the processing device 140 may update the target time phase based on the updated heart disorder of the heart determined based on the second ECG signals (from the plurality of channels) monitored during the scan operation.

In some embodiments, the target time phase may be set according to a default setting of the imaging system 100 or preset by a user (e.g., a doctor) via the terminal device 130. For example, if the target time phase is a time point, the target time phase may be predetermined as 20% R-R, 30% R-R, 40% R-R, 50% R-R, 60% R-R, 70% R-R, etc. As another example, if the target time phase is a time period including two or more time points, the target time phase may be predetermined as 10-30% R-R, 30-50% R-R, 50-70% R-R, 40-60% R-R, 40-70% R-R, etc. In some embodiments, the target time phase may be adjusted according to different scenarios. For example, when the imaging device 110 scans hearts of different subjects, the target time phase may be adjusted to be higher or lower correspondingly. As another example, if a user selects another characteristic wave via the terminal device 130, the target time phase may be adjusted correspondingly.

It should be noted that because coronary arteries including the left and right coronary arteries are distributed in different areas on the surface of the heart, the movement of various structures of the heart may be inconsistent. For example, the movement of the right coronary artery is the fastest, followed by the left circumflex coronary artery, the left main trunk, and the left anterior descending branch. For a certain structure (e.g., a branch), there is always a time phase at which the movement of the structure is slowest. In such cases, the target time phase may be determined in the cardiac cycle(s), and the image quality of cardiac images corresponding to the target time phase may be improved.

In 860, the processing device 140 (e.g., the gating delay and gating width determination module 680) may determine a gating delay and a gating width based on the target time phase.

As used herein, a gating delay refers to a delay time with respect to a time point at which a gating signal is generated. A scan starting time point of the current scanning cycle may be a time point that is later than the starting time point of the current scanning cycle by the gating delay. That is, after the delay time of gating delay later than being triggered by the gating signal, the emission of the radioactive rays may be started. A gating width refers to a time period (after the gating delay) in which the scan operation is performed on the heart by the imaging device. In some embodiments, the gating width may also be referred to as a data acquisition window, i.e., a time period during which scan data can be generated and acquired.

In some embodiments, the gating delay and the gating width of the current cardiac cycle may be determined based on a duration of a previous cardiac cycle. For example, if the duration of a cardiac cycle previous to the current cardiac cycle is 1 second, and the target time phase is 50-60% R-R, then the gating delay may be determined as 500 milliseconds, and the gating width may be determined as 500-600 milliseconds. In some embodiments, the gating delay and the gating width of the current cardiac cycle may be determined based on a plurality of durations corresponding to a plurality of cardiac cycles previous to the current cardiac cycle. For example, the processing device 140 may obtain the plurality of durations corresponding to the plurality of cardiac cycles previous to the current cardiac cycle (e.g., 5, 6, or 7 previous cardiac cycles), determine an average duration of the plurality of durations corresponding to the plurality of previous cardiac cycles, and determine the gating delay and the gating width based on the average duration and the target time phase.

In some embodiments, the gating delay and/or the gating width may be adjusted according to different scenarios. For example, during the scan operation, the heart rate of the subject may accelerate due to short breath holds (or the subject suffers from arrhythmia), which shortens the cardiac cycle (i.e., the R-R interval). If the gating delay and/or the gating width is not adjusted, the scan may cross a cardiac systolic period and a cardiac diastolic period, which causes the motion blur. The motion blur may degrade the quality of reconstructed image(s). Therefore, the gating delay and/or the gating width may be adjusted dynamically, thereby improving the quality of the reconstructed image(s).

In 870, the gating system 170 (e.g., the gating signal determination module 630) and the processing device 140 (e.g., the gating delay and gating width determination module 680) may cooperate to trigger an imaging device to scan the heart based on the gating signal, the gating delay, and the gating width.

The processing device 140 may send a control instruction including the gating delay and the gating width to the controller 160. Upon receiving the gating signal transmitted from the gating system 170 and the gating delay and the gating width transmitted from the processing device 140, the controller 160 may control the excitation source of the imaging device (e.g., an X-ray tube of a CT device) based on the gating signal, the gating delay, and the gating width. Specifically, in the current scanning cycle, in response to the gating signal, the scan operation may be performed on the heart (for a time period corresponding to the gating width) after the gating delay (e.g., 200 ms, 400 ms, or 600 ms). After the time period of the gating delay, the excitation source of the imaging device may be automatically turned on and hold for a time period of the gating width. Alternatively, the controller 160 may control the imaging device for turning on the excitation source of the imaging device for the time period of the gating width (i.e., operating the imaging device 110 to begin the scan). During the scan, the imaging device 110 may generate scan data. The processing device 140 may reconstruct one or more cardiac images based on the generated scan data.

Accordingly, under the prospective gating mode, by identifying (or updating) the target channel of ECG signal, a channel of ECG signal that is unavailable may be automatically switched to another channel that is useable before or during the scan operation, thereby reducing the radiation dose received by the subject and improving the scanning efficiency.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be omitted and/or one or more additional operations may be added. For example, operations 840, 850, and 860 may be omitted. As another example, the process 800 may further include an additional operation to transmit the cardiac image to a terminal device (e.g., a terminal device 130) for display.

Figure 9:
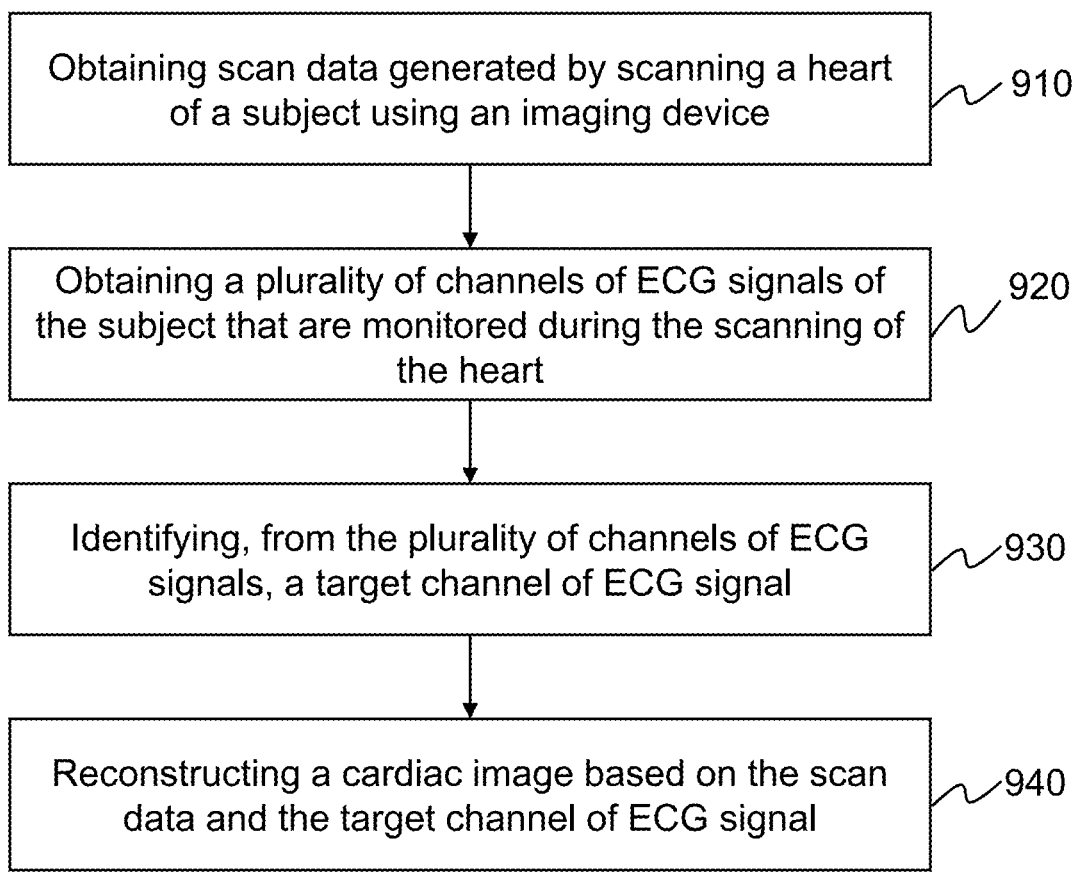
FIG. 9 is a flowchart illustrating an exemplary process for reconstructing one or more cardiac images according to some embodiments of the present disclosure.

FIG. 9 is a flowchart illustrating an exemplary process for reconstructing one or more cardiac images according to some embodiments of the present disclosure. At least a portion of process 900 may be implemented on the computing device 200 as illustrated in FIG. 2 or the mobile device 300 as illustrated in FIG. 3. In some embodiments, one or more operations of process 900 may be implemented in the imaging system 100 as illustrated in FIG. 1. For example, a portion of process 900 may be stored in the storage module 640 of the gating system 170 in the form of instructions, and invoked and/or executed by the gating system 170. As another example, another portion of process 900 may be stored in the storage module 695 of the processing device 140 in the form of instructions, and invoked and/or executed by the processing device 140. The operations of the illustrated process presented below are intended to be illustrative. In some embodiments, the process 900 may be accomplished with one or more additional operations not described, and/or without one or more of the operations discussed. Additionally, the order of the operations of the process 900 illustrated in FIG. 9 and described below is not intended to be limiting. The process 900 may be associated with a scan operation under a retrospective gating mode.

In 910, the processing device 140 (e.g., the acquisition module 650) may obtain scan data generated by scanning a heart of a subject using an imaging device.

The imaging device (e.g., the imaging device 110) may scan the heart of the subject to generate the scan data. In some embodiments, the scan data may be stored in a storage medium (e.g., the storage device 150). The processing device 140 may obtain the scan data from the storage medium. In some embodiments, the processing device 140 may directly obtain the scan data in real time from the imaging device during the scanning of the heart.

In 920, the gating system 170 (e.g., the acquisition module 610) may obtain a plurality of electrocardiogram (ECG) signals of the subject that are monitored during the scanning of the heart. During the scan operation, the scan data and the plurality of channels of ECG signals of the heart may be captured synchronously. For example, the gating system 170 may obtain the plurality of ECG signals in real time or substantially real time during the scan operation and store the plurality of ECG signals in the storage module 640. The generation or collection of the scan data by the imaging device 110 and the monitoring of the plurality of ECG signals by the gating system 170 may be performed simultaneously. More descriptions regarding the plurality of channels of ECG signals may be found elsewhere in the present disclosure (e.g., FIG. 7 and the descriptions thereof).

It should be noted that because the scan data and the plurality of channels of ECG signals of the heart are acquired synchronously, the scan data and the plurality of channels of ECG signals may be matched based on their time information. Thus, the scan data may be divided into a plurality of data sets each of which corresponds to a phase of an ECG signal (or a time period or a time point in each cardiac cycle associated with the ECG signal).

In 930, the gating system 170 (e.g., the target channel determination module 620) may identify a target channel of ECG signal from the plurality of channels of ECG signals. In some embodiments, an amplitude of a characteristic wave of the target channel of ECG signal may be the maximum amplitude among amplitudes of corresponding characteristic waves of the plurality of channels of ECG signals. Operation 930 may be similar to operation 720 of process 700 described above, the descriptions of which may be found in the present disclosure in connection with FIG. 7. The gating system 170 may transmit the target channel of ECG signal to the processing device 140 for image reconstruction.

In 940, the processing device 140 (e.g., the reconstruction module 690) may reconstruct a cardiac image based on the scan data and the target channel of ECG signal.

The processing device 140 may determine target scan data from the scan data based on the target channel of ECG signal. The target scan data may include scan data corresponding to a target time phase associated with the target channel of ECG signal.

In some embodiments, the target time phase may be set according to a default setting of the imaging system 100 or preset by a user (e.g., a doctor) via the terminal device 130. In some embodiments, the target time phase may be determined based on a heart disorder of the heart as described in connection with operation 840 in FIG. 8. For example, the processing device 140 may determine the heart disorder of the heart based at least in part on one or more features of the plurality of channels of ECG signals. The processing device 140 may query a library including a relationship between one or more heart disorders and one or more time phases based on the heart disorder of the heart. The processing device 140 may determine the target time phase based on the query result. In some embodiments, the target time phase may be adjusted according to different scenarios. For example, when the imaging device 110 scans hearts of different subjects, the target time phase may be adjusted to be higher or lower correspondingly. As another example, if a user selects another characteristic wave via the terminal device 130, the target time phase may be adjusted correspondingly.

The processing device 140 may reconstruct the cardiac image based on the target scan data. Exemplary image reconstruction techniques may include a filtered back projection (FBP), a convolutional back projection (CBP), an algebraic reconstruction technology (ART), a statistical reconstruction (SR) algorithm, etc. It should be understood by those skilled in the art that the image reconstruction technique may be varied. All such variations are within the scope of the present disclosure.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be omitted and/or one or more additional operations may be added. For example, operation 910 and operation 920 may be combined into a single operation. As another example, one or more other optional operations (e.g., a preprocessing operation) may be added before operation 930. In some embodiments, the preprocessing operation on the scan data and/or the ECG signals may include a denoising operation, an amplifying operation, a filtering operation, or the like, or any combination thereof. As a further example, the process 900 may include an additional operation to transmit the cardiac image to a terminal device (e.g., a terminal device 130) for display.

FIGS. 10A-10C illustrate exemplary ECG signals corresponding to leads I, II, and III of three human hearts according to some embodiments of the present disclosure.

FIG. 10A shows three ECG signals 1010a, 1020a, and 1030a of leads I, II, and III of a healthy human heart. As illustrated in FIG. 10A, each ECG signal of the healthy human heart has a QRS complex in each cardiac cycle as described in FIG. 5A. For each cardiac cycle, the ECG signal 1020a of lead II has an R-wave (i.e., R-wave 1022a) with a maximum amplitude among the R-waves (i.e., R-waves 1012a, 1022a, and 1032a) of ECG signals 1010a, 1020a, and 1030a of leads I, II, and III. The amplitude of the R-wave of the ECG signal 1020a is the maximum amplitude among amplitudes (absolute values of amplitudes) of other waves (e.g., the Q-wave, the S-wave, etc.) of the three ECG signals 1010a, 1020a, and 1030a. Thus, the R-wave may be designated as a characteristic wave, and the ECG signal 1020a of lead II may be designated as a target channel of ECG signal. Under a prospective gating mode, an imaging device may be caused to perform a scan operation on the healthy human heart based on the lead II ECG signal monitored during the scan operation.

FIG. 10B shows a portion of three ECG signals 1010b, 1020b, and 1030b of leads I, II, and III of a first abnormal human heart. As illustrated in FIG. 10B, for each cardiac cycle, the ECG signal 1010b of lead I has an R-wave (i.e., R-wave 1012b) with a maximum amplitude among the R-waves (i.e., R-waves 1012b, 1022b, and 1032b) of ECG signals 1010b, 1020b, and 1030b of leads I, II, and III. The ECG signal 1030b of lead III has an S-wave (i.e., S-wave 1034b) with a maximum amplitude among the S-waves (i.e., S-waves 1014b, 1024b, and 1034b) of ECG signals 1010b, 1020b, and 1030b of leads I, II, and III. In such cases, a gating signal for scanning the first abnormal heart may be determined based on the ECG signal 1010b of lead I or the ECG signal 1030b of lead III. If the R-wave is specified as the characteristic wave, the gating signal may be generated based on the ECG signal 1010b of lead I. In some embodiments, an ECG signal (i.e., the ECG signal 1030b of lead III) with a maximum amplitude among all the waves of the three ECG signals 1010b, 1020b, and 1030b may be determined as the target channel of ECG signal.

In some embodiments, a target time phase associated with the gating signal may be determined based on the three ECG signals 1010b, 1020b, and 1030b. By comparing the ECG signals of the first abnormal human heart with the ECG signals of the healthy human heart, it can be seen that the three ECG signals of the first abnormal human heart have one or more first features including: (1) the QRS complexes of both the ECG signal 1020b of lead II and the ECG signal 1030b of lead III represent an rS pattern (e.g., a relatively small positive wave (r), and followed by a relatively large negative wave (S)); (2) the amplitude of S-wave 1034b of lead III is greater than the amplitude of S-wave 1024b of lead II; (3) the QRS complex of the ECG signal 1010b of lead I represents a qR pattern (e.g., a relatively small negative wave (q) and followed by a relatively large positive wave (R)); and (4) the QRS axis (or mean QRS axis) is leftward. According to the one or more first features, a first heart disorder of the first abnormal human heart may be determined as a disease relating to the left anterior descending artery (LAD). The target time phase may be determined based on the first heart disorder of the first abnormal human heart. For example, if the R-wave is specified as the characteristic wave (i.e., the ECG signal 1010b of lead I is designated as the target channel of ECG signal), the target time phase may be determined by querying a library (e.g., as illustrated in Table 1) based on the first heart disorder of the first abnormal human heart. The library may include a relationship between one or more heart disorders and one or more target time phases. According to Table 1, the target time phase for the first abnormal human heart may be determined as 60-70% R-R interval.

TABLE 1

An Exemplary Library

| Heart disorder | Target time phase |
|---|---|
| Left anterior descending artery | 60-70% R-R interval |
| Left coronary circumflex descending branch | 50-60% R-R interval |
| Right anterior descending artery | 40-50% R-R interval |
| Normal state | 35-75% R-R interval |

FIG. 10C shows three ECG signals 1010c, 1020c, and 1030c of leads I, II, and III of a second abnormal human heart. As illustrated in FIG. 10C, for each cardiac cycle, the R-waves of the ECG signal 1020c of lead II and the ECG signal 1030c of lead III are almost unidentifiable. The ECG signal 1030c of lead III has a Q-wave (i.e., Q-wave 1036c) with a maximum amplitude among the Q-waves of ECG signals 1010c, 1020c, and 1030c of leads I, II, and III. In such cases, a gating signal for scanning the second abnormal heart may be determined based on the ECG signal 1010c of lead I or the ECG signal 1030c of lead III. For example, if the R-wave is specified as the characteristic wave, the gating signal may be generated based on the ECG signal 1010c of lead I. As another example, if the Q-wave is specified as the characteristic wave, the gating signal may be generated based on the ECG signal 1030c of lead III.

In some embodiments, a target time phase associated with the gating signal may be determined based on the three ECG signals 1010c, 1020c, and 1030c. By comparing the ECG signals of the second abnormal human heart with the ECG signals of the healthy human heart, it can be seen that the three ECG signals of the second abnormal human heart have one or more second features including: (1) the width of S-wave 1014c of lead I is increased (e.g., greater than 0.04 seconds); and (2) the QRS complexes of the three ECG signals 1010c, 1020c, and 1030c lasts more than 0.12 seconds. According to the one or more second features, a second heart disorder of the second abnormal human heart may be determined as a disease relating to the right anterior descending artery. If the R-wave is specified as the characteristic wave (i.e., the ECG signal 1010c of lead I is designated as the target channel of ECG signal), by querying the library as illustrated in Table 1, the target time phase for the second abnormal human heart may be determined as 40-50% R-R interval.

Figure 11:
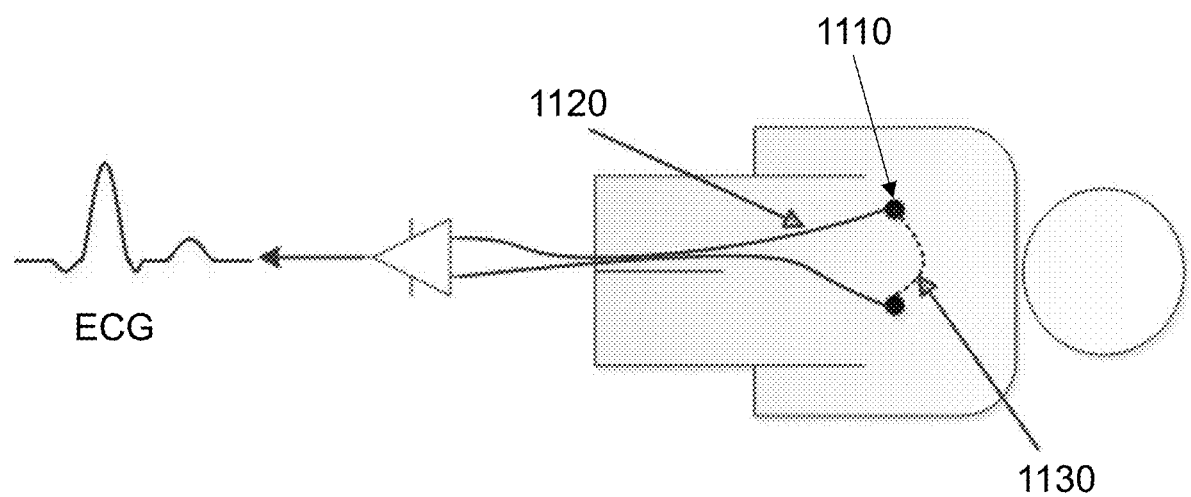
FIG. 11 is a schematic diagram of an ECG signal measurement process according to some embodiments of the present disclosure.

FIG. 11 is a schematic diagram of an ECG signal measurement process according to some embodiments of the present disclosure. As illustrated in FIG. 11, an ECG electrode may include an electrode clamp 1110 and an electrode wire 1120. Two electrodes may form a bipolar limb lead (e.g., leads I, II, and III as illustrated in FIGS. 4A and 4B). During the measurement of an ECG signal, the two electrodes and the subject (e.g., a portion of the skin 1130 of human body) may form a closed loop. The ECG signal may be monitored based on the change of electrical potential difference with time between the two electrodes.

Figure 12A:
FIG. 12A is a schematic diagram of an ECG signal measurement process in a changing magnetic field according to some embodiments of the present disclosure.
Figure 12B:
FIG. 12B is a schematic diagram of an ECG signal measurement process in another changing magnetic field according to some embodiments of the present disclosure.

FIG. 12A is a schematic diagram of an ECG signal measurement process in a changing magnetic field according to some embodiments of the present disclosure. FIG. 12B is a schematic diagram of an ECG signal measurement process in another changing magnetic field according to some embodiments of the present disclosure. If the magnetic field perpendicular to the subject changes (e.g., a y-axis magnetic field needs to be changed to achieve spatial encoding during an MRI scan), the changed magnetic field may pass through a closed loop formed by two electrodes and the subject. According to Faraday's law of electromagnetic induction, an induced current may be generated in the closed loop. For example, as illustrated in FIG. 12A, if the changing magnetic field decreases in the direction perpendicular to the paper surface outward, an induced current in a counterclockwise direction (denoted by arrow M) may be generated in the closed loop. As another example, as illustrated in FIG. 12B, if the changing magnetic field decreases in the direction perpendicular to the paper surface inward, the induced current in a clockwise direction (denoted by arrow M) may be generated in the closed loop. The induced current may cause noises in the monitoring of ECG signal.

In some embodiments, during an MRI scan, in order to reduce the noise signal caused by the induced current, the electrode wire may be winded to form one or more first coils (e.g., first coils 1324 in FIG. 13) and one or more second coils (e.g., second coils 1326 in FIG. 13) with different winding directions (e.g., two opposite winding directions). Specifically, since the y-axis magnetic field is a non-uniformly changing magnetic field, the induced current may be an alternating current. When the induced current (e.g., the alternating current) flows through the first coils and the second coils formed by the electrode wire, a first induced magnetic field may be generated based on each first coil and a second induced magnetic field may be generated based on each second coil. Because the one or more first coils and the one or more second coils have different winding directions, the first induced magnetic field corresponding to each first coil and the second induced magnetic field corresponding to each second coil may have different directions (e.g., two opposite directions indicated by the dotted arrows 1332 and 1334 in FIG. 13). As a result, the first induced magnetic fields generated based on the first coils and the second induced magnetic fields generated based on the second coils may counteract at least a portion of the induced magnetic field generated by the electrode wire, thereby weakening the induced current in turn and reducing the noise of ECG signal caused by the y-axis gradient signal (or y-axis gradient magnetic field). More descriptions regarding the electrode wire may be found elsewhere of the present disclosure (e.g., FIGS. 13-16, and the descriptions thereof).

Figure 13:
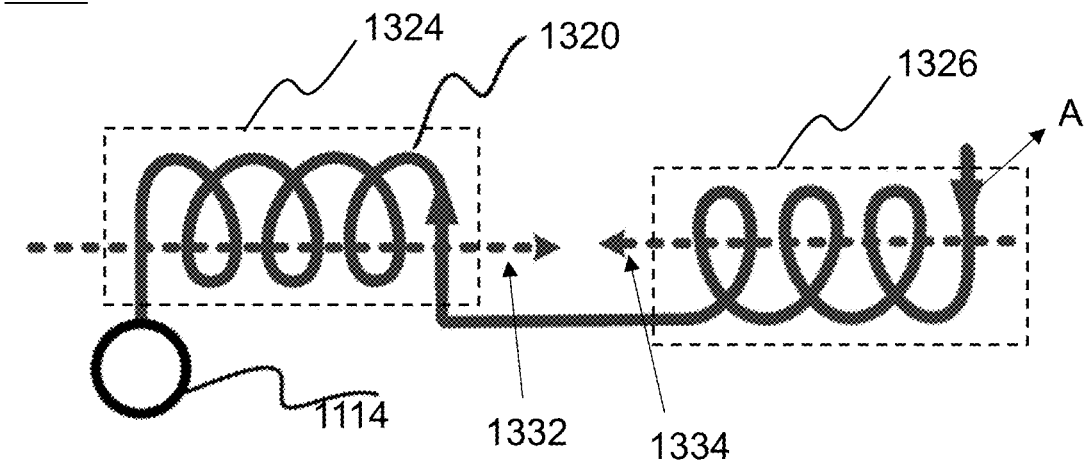
FIG. 13 is a schematic diagram illustrating an exemplary electrode of an ECG lead according to some embodiments of the present disclosure.

FIG. 13 is a schematic diagram illustrating an exemplary electrode of an ECG lead according to some embodiments of the present disclosure. As illustrated in FIG. 13, an electrode 1300 may include an electrode clamp 1310 and an electrode wire 1320 (denoted as solid line). The electrode wire 1320 may be winded into one or more first coils 1324 and one or more second coils 1326. A first winding direction (e.g., a clockwise direction) of each first coil 1324 may be different from a second winding direction (e.g., a counterclockwise direction) of each second coil 1326. For illustration purposes, the winding directions of the one or more first coils 1324 being the same, and the winding directions of the one or more second coils 1326 being the same may be taken as an example. In some embodiments, the first winding direction may be opposite to the second winding direction.

When an ECG signal detector including the electrode 1300 monitors an ECG signal in a changing magnetic field, an induced current (e.g., indicated by arrow A in FIG. 13) may be generated in the electrode wire 1320. In such cases, based on the same basis principle illustrated in FIGS. 12A and 12B, the one or more first coils 1324 may generate a first total induced magnetic field (indicated by the dotted arrow 1332), and the one or more second coils 1326 may generate a second total induced magnetic field (indicated by the dotted arrow 1334). The first total induced magnetic field 1332 may have a direction different from the second total induced magnetic field 1334. As a result, the first total induced magnetic field 1332 and the second total induced magnetic field 1334 may be at least partly counteracted, thereby weakening the induced current in turn and reducing noise in the monitored ECG signal.

In some embodiments, a number of turns of the first coils 1324 may be the same as or different from a number of turns of the second coils 1326. It should be noted that if the diameters of the first coils are uniform, then the first total induced magnetic field 1332 of the first coils 1324 may be proportional to the number of turns of the first coils 1324. If the diameters of the second coils are uniform, then the second total induced magnetic field 1334 of the second coils 1326 may be proportional to the number of turns of the second coils 1326. Therefore, in order to make the first total induced magnetic field 1332 generated by the first coils 1324 and the second total induced magnetic field 1334 generated by the second coils 1326 counteract each other as much as possible, the first total induced magnetic field 1332 needs to be the same (or substantially the same) as the second total induced magnetic field 1334. As a result, the number of turns of the first coils 1324 may be the same (or substantially the same) as the number of turns of the second coils 1326.

In some embodiments, the one or more first coils 1324 and the one or more second coils 1326 may be arranged in various ways according to actual needs. For example, the one or more first coils 1324 and the one or more second coils 1326 may form a plurality of coil sets. The plurality of coil sets may be arranged sequentially in a same direction. As another example, a portion of the plurality of coil sets may be arranged sequentially in a same direction to form a first coil group, and the remaining coil sets may be arranged sequentially in the same direction to form a second coil group. The first coil group may surround the second coil group. In such cases, a diameter of each coil in the first coil group may be greater than a diameter of each coil in the second coil group. In some embodiments, an insulation layer may be provided between the first coil group and the second coil group. In some embodiments, a first coil set may include the one or more first coils 1324, and a second coil set may include the one or more second coils 1326. The first coil set and the second coil set may be arranged in an arrangement illustrated in FIG. 13. In some embodiments, a coil set may include a first coil and a second coil, and the plurality of coil sets may be arranged sequentially in the same direction. That is, the one or more first coils 1324 and the one or more second coils 1326 may be arranged alternately. As another example, a coil set may include "m" turns of the first coils 1324 and "n" turns of the second coils 1326, wherein "m" and "n" denote integers greater than or equal to 1.

The electrode wire 1320 may include an insulation sheath and a wire core for conducting a current. In some embodiments, the electrode core may be made of a material including metal, alloy, carbon element, composite metal, or the like, or any combination thereof. For example, the electrode core may be made of metallic line or carbon fiber. In some embodiments, the insulation sheath may be made of a material including rubber, plastic, carbon fiber, boron fiber, aromatic polyamide fiber, or the like, or any combination thereof.

Figure 14:
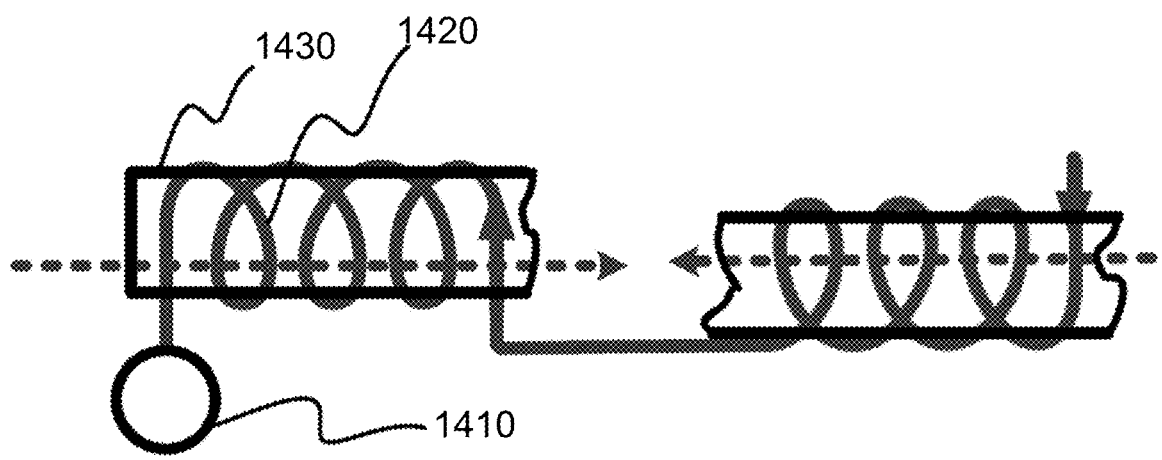
FIG. 14 is a schematic diagram illustrating an exemplary electrode of an ECG lead according to some embodiments of the present disclosure.

FIG. 14 is a schematic diagram illustrating an exemplary electrode of an ECG lead according to some embodiments of the present disclosure. The electrode 1400 may be similar to the electrode 1300 as described in FIG. 13. For example, as illustrated in FIG. 14, the electrode 1400 may include an electrode clamp 1410 and an electrode wire 1420. As another example, the electrode wire 1420 may be winded into one or more first coils and one or more second coils. A first winding direction of each first coil may be different from a second winding direction of each second coil.

The electrode 1400 may further include an insulation support 1430 configured to support at least one portion of the one or more first coils and the one or more second coils. For example, the electrode wire 1420 may be spirally winded on the insulation support 1430 to form the one or more first coils and the one or more second coils. In such cases, the one or more first coils and the one or more second coils may not easily be deformed, thereby extending the service life of the electrode 1400. In some embodiments, the insulation support 1430 may be made of a material including rubber, plastic, carbon fiber, boron fiber, aromatic polyamide fiber, or the like, or any combination thereof.

Figure 15:
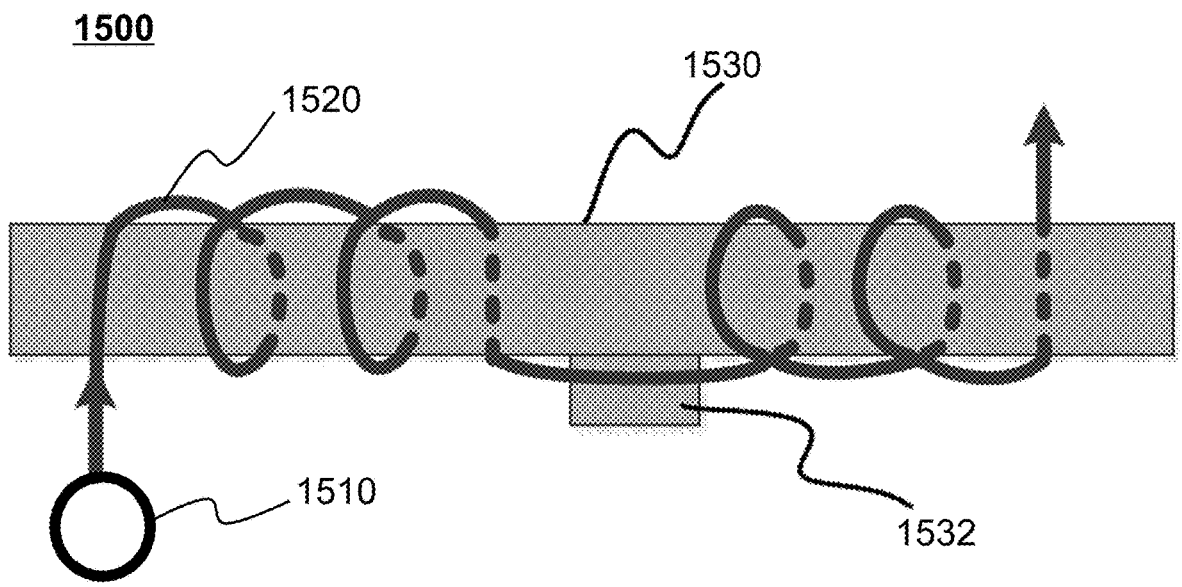
FIG. 15 is a schematic diagram illustrating an exemplary electrode of an ECG lead according to some embodiments of the present disclosure.

FIG. 15 is a schematic diagram illustrating an exemplary electrode of an ECG lead according to some embodiments of the present disclosure. The electrode 1500 may be similar to the electrode 1400 as described in FIG. 14. For example, as illustrated in FIG. 15, the electrode 1500 may include an electrode clamp 1510, an electrode wire 1520, and an insulation support 1530. As another example, the electrode wire 1520 may be winded into one or more first coils and one or more second coils. A first winding direction of each first coil may be different from a second winding direction of each second coil.

The electrode 1500 may further include one or more fixing clips 1532. The one or more fixing clips 1532 may be disposed on the surface of the insulation support 1530 and be configured to fix an end of at least one coil of the coils (e.g., the one or more first coils and one or more second coils). It should be noted that if the electrode wire 1520 is winded to form the first coils and the second coils, the ends between a first coil and an adjacent second coil may be easy to loosen, which brings inconvenience to the winding process and the usage of the electrode 1500. In such cases, by using the one or more fixing clips 1532, an end of a first coil and a corresponding end of an adjacent second coil may be fastened, so that the one or more first coils and the one or more second coils may not easily be deformed, thereby further extending the service life of the electrode 1500. In some embodiments, the one or more fixing clips 1532 may be made of a material including rubber, plastic, carbon fiber, boron fiber, aromatic polyamide fiber, or the like, or any combination thereof. The material of the one or more fixing clips 1532 may be the same as or different from the material of the insulation support 1530.

Figure 16:
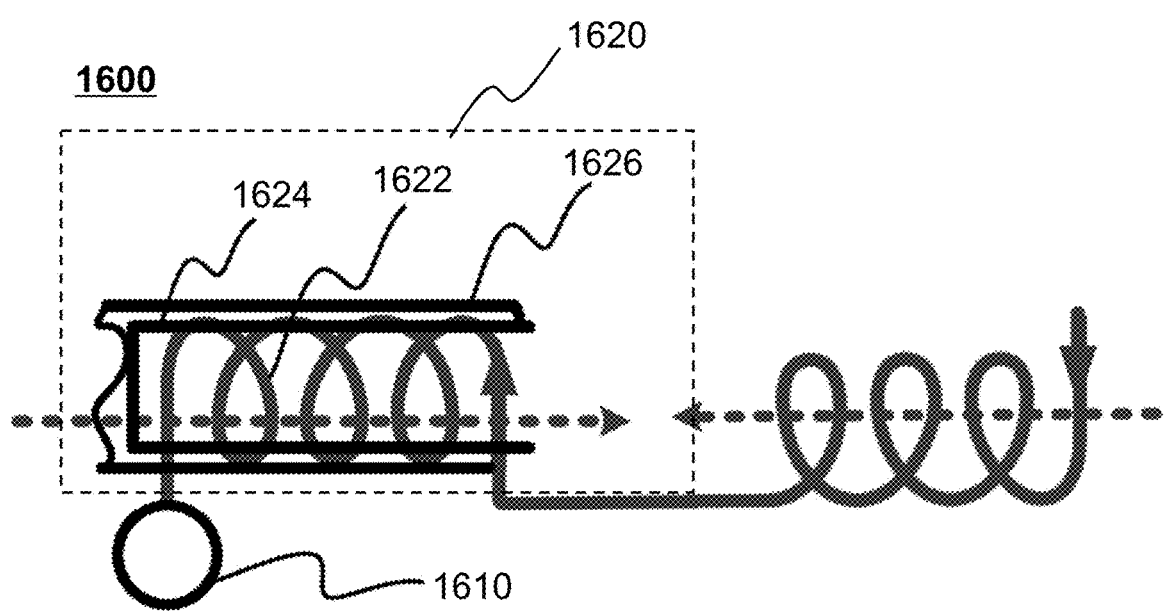
FIG. 16 is a schematic diagram illustrating an exemplary electrode of an ECG lead according to some embodiments of the present disclosure.

FIG. 16 is a schematic diagram illustrating an exemplary electrode of an ECG lead according to some embodiments of the present disclosure. As illustrated in FIG. 16, an electrode 1600 may include an electrode clamp 1610 and an electrode wire 1620.

The electrode wire 1620 may include a wire core 1622, an insulation support 1624 and a protective sheath 1626. The wire core 1622 may be winded into one or more first coils and one or more second coils. A first winding direction of each first coil may be different from a second winding direction of each second coil. The insulation support 1624 may be configured to support at least one portion of the one or more first coils and the one or more second coils. For example, a portion of the wire core 1622 may be spirally winded on the insulation support 1624 to form the one or more first coils and the one or more second coils. In some embodiments, the insulation support 1624 may be made of a material that has good insulation, high strength, good toughness, etc. For example, the material may include rubber, plastic, carbon fiber, boron fiber, aromatic polyamide fiber, or the like, or any combination thereof. The protective sheath 1626 may be configured to cover the wire core 1622 and the insulation support 1624 to form the electrode wire 1620. In some embodiments, the protective sheath 1626 may be made of a material that is the same as the material of the insulation support 1624.

In some occasions, even after the first coils and/or the second coils are formed on the insulation support 1624, if the ends between a first coil and an adjacent second coil are merely compressed and fixed by the protective sheath 1626, the adjacent coils may be easily loosen and severely deformed, thereby affecting the service life of the electrode 1600. Therefore, the electrode 1600 may further include one or more fixing clips (not shown). The one or more fixing clips may be disposed on the surface of the insulation support 1624 and be configured to fix an end of at least one coil of the coils (i.e., the one or more first coils and one or more second coils). In such cases, the one or more first coils and the one or more second coils may not easily be deformed, thereby further extending the service life of the electrode 1600.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure, or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures, or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer-readable program code embodied thereon.

A non-transitory computer-readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer-readable signal medium may be any computer-readable medium that is not a computer-readable storage medium and that may communicate, propagate, or transport a program for use by or in connection with an instruction execution system, apparatus, or device. Program code embodied on a computer-readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python, or the like, conventional procedural programming languages, such as the "C" programming language, Visual Basic, Fortran, Perl, COBOL, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate" or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system for medical imaging, comprising:
at least one storage device storing executable instructions, and at least one processor in communication with the at least one storage device, when executing the executable instructions, causing the system to perform operations including: obtaining a plurality of channels of electrocardiogram (EGG) signals of a heart of a subject, the plurality of channels of EGG signals includes a predetermined channel of EGG signal;
switching the predetermined channel to a target channel when the predetermined channel of EGG signal is detected to be unavailable in a scan operation, wherein the switching the predetermined channel to a target channel when the predetermined channel of ECG signal is detected to be unavailable in a scan operation includes;
identifying, from the plurality of channels of ECG signals, the target channel of ECG signal;
switching the predetermined channel to the target channel when the predetermined channel of ECG signal is detected to be unavailable in a scan operation; wherein the identifying, from the plurality of channels of ECG signals, the target channel of EGG signal includes;
performing a preprocessing operation on each of the plurality of channels of EG signals; and
determining, from the plurality of channels of preprocessed EGG signals, the target channel of EGG signal;
wherein an amplitude of a characteristic wave of the target channel of EGG signal is the maximum amplitude among amplitudes of corresponding characteristic waves of the plurality of channels of EGG signals—and causing, based on the switched channel of EGG signal, an imaging device to perform the scan operation on the heart of the subject.

2. The system of claim 1, wherein the preprocessing operation includes at least one of an amplifying operation or a filtering operation.

3. The system of claim 1, wherein the causing, based on the switched channel of ECG signal, an imaging device to perform the scan operation on the heart of the subject includes:
generating, based on the switched channel of ECG signal, a gating signal; and
causing, based on the gating signal, the imaging device to perform the scan operation on the heart of the subject.

4. The system of claim 3, wherein the generating, based on the switched channel of ECG signal, a gating signal includes:
detecting the characteristic wave of the switched channel of ECG signal; and
generating, based on the characteristic wave of the switched channel of ECG signal, the gating signal.

5. The system of claim 3, wherein the at least one processor is further configured to cause the system to perform additional operations including:
determining, based at least in part on the plurality of channels of ECG signals, a heart disorder of the heart; and
determining, based on the heart disorder of the heart, a target time phase;
determining, based on the target time phase, a gating delay and a gating width; and
the causing, based on the gating signal, the imaging device to perform the scan operation on the heart of the subject includes:
causing, based on the gating signal, the gating delay, and the gating width, the imaging device to perform the scan operation on the heart of the subject.

6. The system of claim 5, wherein the determining, based on the heart disorder of the heart, a target time phase includes:
querying a library based on the heart disorder of the heart to obtain a query result, the library including a relationship between the heart disorder of the heart and the target time phase; and
determining the target time phase based on the query result.

7. The system of claim 5, wherein the determining, based on the target time phase, a gate delay and a gating width includes:
obtaining a plurality of durations corresponding to a plurality of previous cardiac cycles before a current cardiac cycle;
determining an average duration of the plurality of durations corresponding to the plurality of previous cardiac cycles; and
determining, based on the average duration and the target time phase, the gating delay and the gating width.

8. The system of claim 5, wherein the at least one processor is further configured to cause the system to perform additional operations including:
obtaining a plurality of channels of second ECG signals monitored during the scan operation;
determining, based at least in part on the second ECG signals, an updated heart disorder of the heart; and
updating, based on the updated heart disorder of the heart, the target time phase.

9. The system of claim 1, wherein a retrospective ECG gating is used in the scan operation, and the at least one processor is further configured to cause the system to perform additional operations including:
obtaining scan data generated in the scan operation;
obtaining, from the switched channel, a second ECG signal monitored during the scan operation; and
reconstructing a cardiac image based on the scan data and the second ECG signal.

10. The system of claim 1, wherein a retrospective ECG gating is used in the scan operation, and the at least one processor is further configured to cause the system to perform additional operations including:
obtaining scan data generated in the scan operation;
obtaining a plurality of channels of second ECG signals monitored during the scan operation; and
reconstructing a cardiac image based on the scan data and the second ECG signals.

11. The system of claim 10, wherein the reconstructing a cardiac image based on the scan data and the second ECG signals includes:
determining, based at least in part on the second ECG signals, a heart disorder of the heart;
determining, based on the heart disorder of the heart, a target time phase;
determining, from the scan data, target scan data corresponding to the target time phase; and
reconstructing, based on the target scan data, the cardiac image.

12. The system of claim 1, wherein the at least one processor is further configured to cause the system to perform additional operations including:
obtaining a plurality of channels of second ECG signals monitored during the scan operation;
determining, based on the second ECG signals, an updated channel of ECG signal; and
operating, based on the updated channel of ECG signal, the imaging device to perform the scan operation on the heart.

13. The system of claim 12, wherein the at least one processor is further configured to cause the system to perform additional operations including:
prompting a user that the channel of ECG signal is updated.

14. The system of claim 1, wherein the plurality of channels of electrocardiogram (ECG) signals are detected by a multi-lead sensing device.

15. The system of claim 14, wherein the multi-lead sensing device includes one or more electrodes, at least one of the one or more electrodes includes an electrode clamp and an electrode wire, wherein:
the electrode wire is winded to form one or more first coils and one or more second coils, a first winding direction of each of the one or more first coils being different from a second winding direction of each of the one or more second coils.

16. The system of claim 5, wherein the determining, based at least in part on the plurality of channels of ECG signals, a heart disorder of the heart includes:
determining one or more features of the plurality of channels of ECG signals; and
determining, based on the one or more features, the heart disorder of the heart.

17. The system of claim 16, wherein the determining, based on the one or more features, the heart disorder of the heart includes:
- querying a library including a relationship between the one or more features and one or more heart disorders based on the one or more features; or
- determining the heart disorder based on a heart disorder identification model.

\* \* \* \* \*